United States Patent [19]
Hogan

[11] Patent Number: 5,279,600
[45] Date of Patent: Jan. 18, 1994

[54] CLOSED, FLUID-MODULATING RECEIVING SYSTEM FOR THE CONVEYANCE, MODULATION, AND COLLECTION OF FLUID MATTER

[75] Inventor: John D. Hogan, Gloucester, Mass.

[73] Assignee: Beth Israel Hospital Assoc. Inc., Boston, Mass.

[21] Appl. No.: 886,404

[22] Filed: May 21, 1992

Related U.S. Application Data

[63] Continuation of Ser. No. 662,639, Feb. 28, 1991, Pat. No. 5,139,493, which is a continuation-in-part of Ser. No. 529,566, May 25, 1990, Pat. No. 5,135,792, which is a continuation-in-part of Ser. No. 445,008, Dec. 4, 1989, Pat. No. 5,061,235, which is a continuation-in-part of Ser. No. 142,077, Jan. 8, 1988, Pat. No. 4,885,000, which is a continuation-in-part of Ser. No. 1,648, Jan. 9, 1987, abandoned.

[51] Int. Cl.$^5$ .............................................. A61M 1/00
[52] U.S. Cl. ..................................... 604/317; 604/328; 604/349
[58] Field of Search ............... 604/317, 322, 327, 331, 604/333, 334, 348, 349, 350, 374

[56] References Cited

U.S. PATENT DOCUMENTS

| | | | |
|---|---|---|---|
| 3,312,221 | 4/1967 | Overment | 604/333 |
| 4,134,404 | 1/1979 | Williams, Jr. | 604/333 |
| 4,512,771 | 4/1985 | Norton | 604/333 |
| 4,702,740 | 10/1987 | Batos | 604/335 |
| 4,790,834 | 12/1988 | Austin | 604/349 |
| 4,820,291 | 4/1989 | Terauchi et al. | 604/349 |
| 5,053,029 | 10/1991 | Yang | 604/374 |
| 5,195,997 | 3/1993 | Carns | 604/349 |

Primary Examiner—David Isabella
Assistant Examiner—Gina M. Gualtieri
Attorney, Agent, or Firm—David Prashker

[57] ABSTRACT

The present invention provides a closed, fluid-modulating receiving system for the conveyance, modulation, and collection of fluid matter from its source. The receiving system may be employed under both in vivo and inanimate use conditions for the collection and disposal of fluids which may be infectious, hazardous, or toxic in and of themselves.

2 Claims, 11 Drawing Sheets

CLOSED, FLUID-MODULATING RECEIVING SYSTEM FOR THE CONVEYANCE, MODULATION, AND COLLECTION OF FLUID MATTER

CROSS-REFERENCE

This is a continuation of application Ser. No. 07/662,639, filed on Feb. 28, 1991, now U.S. Pat. No. 5,139,493 which is a Continuation-In-Part of U.S. patent application Ser, No. 529,566 filed May 25, 1990, now U.S. Pat. No. 5,135,792; which is a Continuation-In-Part of U.S. patent application Ser. No. 445,008 filed Dec. 4, 1989 now U.S. Pat. No. 5,061,235; which is a Continuation-In-Part of U.S. patent application Ser. No. 142,077 filed Jan. 8, 1988 now U.S. Pat. No. 4,885,000; which is a Continuation-In-Part of U.S. patent application Ser. No. 001,648 filed Jan. 9, 1987, now abandoned.

FIELD OF THE INVENTION

The present invention is concerned generally with articles and methods for removing fluids from various sources; and is particularly directed to receiving systems for the conveyance,, modulation, collection, and disposal of fluid matter from its source under both in vivo and inanimate conditions.

BACKGROUND OF THE INVENTION

In this advanced technological age, the collection and disposal of fluids, particularly waste fluids, has become an ever more complex problem of increased difficulty. In its most general usage, the term "fluid matter" includes not only those substances in a true liquid physical state but also includes substances in solid physical state which are suspended, dispersed, or dissolved in a liquid carrier; as well as those compositions which exist or have been converted into a vaporized or gaseous state. Accordingly, the term "fluid matter" encompasses and denotes any and all of these possible combinations and permutations.

Much of the difficulty and complexity regarding the collection and disposal of fluid matter in general and of waste fluid matter in particular centers and focuses upon what are the proper answers to two different, but directly related, fundamental questions. These are: First, how does one collect and dispose of the fluid matter without himself also coming into effective contact with or being detrimentally affected by the fluid matter during the collection and disposal process? Second, how does one effectively collect and dispose of the fluid matter without concomitantly influencing, contaminating, and/or otherwise altering the source from which the fluid matter originates? Ironically, a satisfactory answer and resolution to one of these questions will typically cause a completely unsatisfactory and often intolerable result with regard to the other of these inquiries. A very few commonplace examples will illustrate the nature and consequences resulting from the longstanding and recurring conflict between the answers to these questions.

Under in vivo conditions, the conflict presented by these fundamental questions is well demonstrated by the persons typically admitted into a hospital ward for: a surgical manipulation or incision; relief from an obstruction or constriction in the urogenital tract; or an ileostomy or colostomy. In the surgical incision instance, a drain is often inserted into the wound area after the surgical procedure in order to collect and drain fluid from the wound subsequently. Conventional practice, however, employs drains having completely open ends in which one open end is inserted into the body of the living subject while the other end lies open and totally exposed to the ambient environment or is superficially covered with a simple bandage. Not surprisingly, infection via the drain at the surgical incision site is commonplace; and is recognized as a frequent hazard and consequence of this procedure. Thus, neither fundamental question is satisfactorily answered, much less mutually resolved, by conventional surgical drains and drainage practices. Not only is the patient (the source) put at risk, but also those persons attending the patient are also unknowingly placed at risk by handling the fluid matter discharged from the drainage tube.

A second in vivo example of a failure to satisfactorily answer and resolve the two fundamental questions is the conventional insertion of a urinary catheter through the genital area into the urinary tract of a patient for relief and release of accumulated urine from the bladder. Typically, a urinary catheter remains inserted internally for several days; and the usual procedure is for a nurse periodically to irrigate the catheter with sterile saline over the duration of its use. However, the catheter, from the time of its insertion internally, must remain completely open and can not prevent backflow of urine from its external end; and unavoidably becomes a pathway for potential infections and other medical complications. Here again, the dangers to both patient and attendant nurse caused by the lack of effective answers to the two fundamental inquiries are apparent. While the collection and disposal of the urinary fluid is physically easy, the nurse or attendant collecting and handling the discharged urine is at serious risk because of unknown bacteria or other microbes which might be in the urine; similarly, the patient is at risk by the continuous exposure of his urinary tract to the presence and possible backflow of urine throughout the entire period of catheter use.

A third in vivo example is the consequence of a (partial or complete) ileostomy or colostomy from which the person must then use a bag for collection of fecal matter. The deficiencies of and problems associated with the conventional ileostomy/colostomy bag are many and attributable to a failure to adequately answer and effectively resolve the two fundamental questions. These deficiencies and problems include: failures of the bag to contain and hold the solid, liquid, and gaseous parts of the fecal matter released from the bowel; severe leakage and drainage both from the resected bowel end and from the retaining bag itself; the frequent infections to the patient at the area of connection between the colostomy bag and the resected end of the bowel; the fecal exposure and general danger to the person attending or helping the patient with attachment and/or replacement of the colostomy bag; and the general inconvenience and cumbersome nature of the conventional colostomy bag, its mode of use, and its mode of attachment and disconnection. Not only is the patient who must use the bag subject to embarrassment, discomfort, and potential infection; often another person aiding the patient is also placed at serious risk by the bag.

Similarly, the two fundamental inquiries apply to a number of commonplace situations at home and in the workplace where the collection and disposal of fluid matter can not be achieved without serious consequences or risks to either the person performing the collection of fluid or the source of the fluid. Typical examples are the use of formalin and/or formaldehyde in the mortuary and funeral home; and the use of organic solvents in the dry cleaning industry. Clearly, both of these instances involve the use of hazardous and/or toxic fluids in which direct exposure whether by direct physical contact or by air contamination may lead to serious chemical and biological injury. Thus, the person collecting and disposing of these hazardous and/or toxic fluids risks his health (and sometimes his life) if the means employed for collecting and disposing of these fluids are not safe and assured. Similarly, if the person does not take effective measures to safeguard the source of these hazardous and/or toxic fluids—recognizing that these fluids have beneficial uses and applications—then by haphazard and reckless methods of collection and disposal, the source may unintentionally and inadvertently become contaminated, chemically altered, or otherwise subjected to undesired change.

It will be recognized and appreciated therefore that the two fundamental questions must be answered and resolved without major conflict; and are of primary importance and paramount interest both to the person performing the task of collecting the fluid and to the source of the fluid matter. The need for an effective system for the collection and disposal of fluid matter which protects and preserves both the source of the fluid as well as the person collecting the fluid is long recognized and remains today unsatisfied in the main. The development of a general receiving, collection, and disposal system which adequately answers and properly resolves these two fundamental issues would therefore be recognized by persons ordinarily skilled in this field as being a major advance and providing highly desirable benefits to the user.

SUMMARY OF THE INVENTION

The present invention provides a closed, fluid-modulating receiving system for the conveyance, modulation, and collection of fluid matter from its source, said fluid-modulating receiving system comprising:

a conduit for the conveyance of fluid matter, said conduit having a closed body of determinable dimensions and configuration, an internal lumen for the flow of fluid matter, and two discrete open ends, one of said open conduit ends to be positioned in flow communication with the source of fluid matter;

a discrete, flow-through modulator unit having at least one fluid-modulating element, a flow inlet, and a flow outlet, said modulator unit being positioned external to the source of fluid matter and being in closed fluid flow communication with said conduit such that all fluid matter conveyed from the source by said conduit flows into contact with and is acted upon by said fluid-modulating element, at least one identifiable property of said fluid matter being acted upon by said fluid-modulating element to yield a resulting fluid product;

a replaceable receiver of determinable dimensions and volume in closed fluid flow communication with said modulator unit for receipt and collection of said resulting fluid product, the internal volume of said receiver being not less than partially filled with at least one superabsorbent fibrous material comprising fluid-absorbing fibers able to absorb at least fifteen times their own weight of liquid, such resulting fluid product as flows into said receiver being at least partially absorbed by said superabsorbent fibrous material.

BRIEF DESCRIPTION OF THE DRAWING

The present invention may be more easily and completely understood when taken in conjunction with the accompanying drawing, in which.

DETAILED DESCRIPTION OF THE INVENTION

Figure 1:
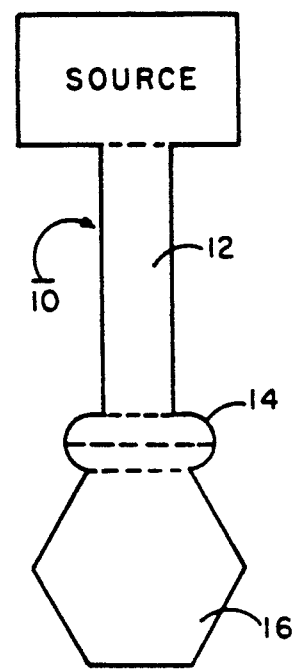
FIG. 1 is a block diagram illustrating the essential component parts of the present invention.

The present invention is a closed receiving system for the conveyance, modulation, collection, and subsequent disposal of fluid matter from its source. The present receiving system is unique in its requisite essential component parts; and is unusual in its ability to receive and collect fluid matter comprising gaseous, liquid, and even solid materials in a manner which protects the user from the fluid matter and concomitantly protects the source of the fluid matter from contamination or exposure to persons or the ambient environment. Among the many benefits and advantages thus provided by the present invention are the following:

1. The receiving system of the present invention after assembly is a completely closed system for the protection of both persons and the source of the collected matter. The assembled receiving system remains closed at all times whether or not the system is in actual use; and remains a closed system even after the fluid matter has been received and collected for disposal. Due to the closed nature of this receiving system, neither the source of the fluid matter initially, nor the means by which the fluid matter is conveyed, nor the received and collected fluid matter ready for disposition lies exposed to the ambient environment at any time.

2. The receiving system of the present invention collects the fluid matter and combines the collected fluid matter with at least one superabsorbent fibrous material comprising fluid-absorbing fibers able to absorb not less than 15 times their own weight of liquid. Accordingly, such fluid matter as flows into the system is collected and becomes at least partially if not entirely absorbed by the superabsorbent fibrous material. The absorbance of the fluid matter in this manner eliminates the usual problems of liquid pressures, surges, sloshing, and the like encountered using conventional collection and storage apparatus; and provides for an easier and more convenient disposition of the absorbed fluid matter without fear of liquid leakage.

3. The closed receiving system comprising the present invention may be employed as a temporary mode of fluid collection or used as a permanently installed fixture for long-term service. Accordingly, the receiving system in any of its various embodiments may be employed for only a few hours or a few days, or alternatively for an indefinite number of years. The system provides for a replaceable receiver of variable dimensions, configuration, and volume to be positioned in closed fluid-flow communication with the source of the fluid matter. The receiver, being not less than partially filled with at least one superabsorbent fibrous material comprising fluid-absorbing fibers, is able to absorb at least 15 and often 60–100 times their own weight of liquid. The system as a whole permits replacement of the receiver as desired or necessary; and typically maintains the remainder of the system in a closed condition during the time required to replace one receiver unit with another. Therefore, whether the receiving system is employed only on a temporary basis or as a permanently installed system, the conveyance, modulation, and collection of fluid matter from its source can continue effectively.

4. The receiving system of the present invention can take form in many different embodiments and optionally includes many desirable features and conveniences for the user. Regardless of the complexity of the embodiment and despite the many diverse forms and constructions which may be employed in the system, only three component parts are required for and essential to the receiving system in order to be both operative and effective. The diversity of embodiments and formats is clearly intended to satisfy and comply with the needs and/or desires of the individual use; and the many alternative forms and applications for the present receiving system are purposely intended and knowingly expected to be divergent and radically remote from one another as often as they are similar. Thus, the closed receiving system has no restrictions or limitations whatsoever regarding its physical design and construction, place and mode of application, or intended use and function beyond those minimal requirements noted herein.

5. The present receiving system is desirably employed in a variety of different in vivo applications and settings for the removal of fluid matter from the body of a living subject, human and animal. Merely illustrative of the diversity of in vivo embodiments for the present invention are the system for receiving drainage fluid from a surgical incision in a living subject; the system for receiving fluid from the urinary tract in a living subject; and the system for receiving fluid fecal matter from a resected bowel in a living subject after ileostomy or colostomy. In addition, due to the intended range and variety of in vivo usages and applications, the entirety of the present receiving system may be prepackaged and/or presterilized prior to use; and employed alternatively as a temporary or as a permanent receiving system in vivo as required.

6. The present receiving system may also be advantageously employed with inanimate articles and non-living equipment for the receipt and collection of fluid matter. Under such use circumstances, the embodiments of the receiving system may be either larger or smaller in size and volume; employ resilient and long-wearing materials such as refractory metals and plastics; and typically be employed in the collection and disposal of waste, hazardous, and/or toxic fluids which are known or are suspected of being foul, dangerous, or lethal to living humans and animals. The embodiments described hereinafter are merely exemplary and illustrative of temporary and permanent receiving systems for the receipt, collection, and subsequent disposal of waste, hazardous, and/or toxic fluids.

7. The receiving system of the present invention permits and optionally provides for chemical reactive contact, chemical modification and/or chemical alteration of the fluid matter while within the confines of the system as part of its ultimate receipt and collection. The site of chemical reaction and modification within the closed receiving system may be varied as the needs or desires of the user demand. Nevertheless, regardless of the site or precise positioning within the closed receiving system, the fluid matter being conveyed and subsequently received and collected can optionally be combined with a variety of reactive chemical substances such as initiators, activators, neutralizers, anti-microbial agents, enzymes, dye reagents, and the like. The chemical composition and formulation, structure, chemical attributes, affinity for specific compounds, and activity properties for the individual chemical compositions (including gaseous, liquid, and solid materials) comprising the fluid matter may be substantially altered, modified, and changed in greater or lesser degree during the time required for passage of the fluid material from its source to final receipt and collection. Thus, under in vivo applications and circumstances, the collected fluid matter may optionally be combined with germicidal agents to reduce or eliminate the potential infectivity of the fluid; and/or with chemical initiators or activators to reduce the nature or chemical activity of the fluid matter; and/or with chemical neutralizing agents to retard or eliminate the corrosive or pervasive chemical properties of the fluid matter. The assembled receiving system, being closed to the ambient environment, allows even for major chemical reaction and alteration of waste, hazardous, and/or toxic fluid substances in a controlled and safeguarded manner such that the collected fluid presents a greatly reduced risk and danger during ultimate disposition.

It will be recognized and appreciated therefore that the receiving system which is the subject matter as a whole comprising the present invention may take physical form in many different embodiments and constructions; and is useful and effective for the receipt and collection of fluid matter in a variety of radically remote and divergent applications and use formats. Thus, in order to provide a clear, complete, and comprehensive understanding of the present invention, the detailed description will be presented hereinafter as follows: a detailed review and disclosure of the individual component parts comprising the present invention which are required and essential in each and every embodiment of the receiving system; three different preferred embodiments of the present invention illustrating the range of intended uses and applications under in vivo conditions; and an additional preferred embodiment of the present receiving system exemplifying the range of intended uses under inanimate/nonliving conditions for the receipt and collection of waste, hazardous, and/or toxic fluid matter.

I. THE REQUIRED AND ESSENTIAL COMPONENT PARTS OF THE RECEIVING SYSTEM

The present invention comprising a closed receiving system for the conveyance, modulation, collection, and subsequent disposal of fluid matter from its source is illustrated by FIG. 1 in block schematic form. The closed receiving system 10 as an assembled whole is comprised of only three essential components: a conduit 12 for the conveyance of fluid matter; a discrete, flow-through modulator unit 14 having at least one fluid-modulating element; and a replaceable receiver 16. As shown by FIG. 1, the source of the fluid matter is in closed fluid flow communication with the conduit 12, with the modulator unit 14, and with the receiver 16. Thus, regardless of the true dimensions, configuration, volume, capacity, materials, or mature of fluid-flow linkage among the requisite component parts, the receiving system 10 schematically illustrated by FIG. 1 provides a closed, in-line, and dead-ended channel of uninterrupted fluid flow between the source of fluid matter initially and the receiver 16 for the collection of fluid at the terminus. A detailed disclosure and description of each essential component part follows:

A. The Conduit

The conduit is an essential component required for enabling the conveyance of fluid matter from its source. The conduit, by definition, serves either or both of two functions and capabilities for the system as a whole. The first function and capability is as a tangible carrier which is in physical contact with the fluid matter and itself carries and conveys the fluid matter directly. The additional or alternative function and capability for the conduit is to serve as a structural connector or link without which the physical passage or transfer of fluid matter from the source would not otherwise occur. The conduit comprises a closed body of determinable dimensions and configuration for the flow of fluid matter and has two discrete open ends. One open end of the conduit is to be positioned in flow communication with the source of fluid matter; the other open end is disposed in fluid-flow communication with the modulator unit.

The primary, although not necessarily exclusive, purpose and function for the conduit is to convey fluid matter from the source to the modulator unit; and accordingly one open conduit end must be able to be positioned in either direct or indirect flow communication with the source of fluid matter. The nature and mode of positioning from an open conduit end with the source of fluid matter will vary greatly with the source itself and the nature of the fluid matter to be conveyed. Thus, the open end of the conduit may in some circumstances actually be inserted into the source itself; under other conditions the open conduit end will surround the source of fluid matter; and, in other circumstances, the open conduit end will merely lie adjacent to or abutt an area or zone in which the fluid accumulates at its source. This is commonly the case under in vivo conditions as exemplified by the embodiments described hereinafter. The other open end of the conduit is in closed fluid flow communication with the modulator unit and, in some meaningful degree, lies external to the source of fluid matter. It will be recognized and appreciated also that the essential requirement is only that the open conduit end be in fluid flow communication rather than be in direct contact or physical juncture with the modulator unit as such. Thus, it is optionally available to the user of the present receiving system to introduce and position one or more extraneous articles or apparatus between the external or remote open end of the conduit and the modulator unit which must ultimately be in-line and in flow communication with the conduit itself. Whether or not there are intervening articles or apparatus positioned between the conduit and the modulator unit is of no importance or consequence to the present receiver system so long as no longstanding or substantive obstruction/interruption in the flow of fluid occurs; and so long as there is no loss of closure or continuity in the fluid flow communication between the conduit and the modulator unit.

Accordingly, it will be recognized and appreciated that the length, size or diameter of internal lumen, configuration, or fluid carrying volume capacity for the conduit is of little consequence or importance. Many different modes of construction and a diverse range of materials are available for making the conduit. Thus, for expected in vivo uses and applications, the conduit typically will be a small or closed tube formed of elastic and flexible materials which can be subjected to heat or steam sterilization without major loss of cohesive properties or tensile strength. Alternatively, under non-living or inanimate use conditions, the conduit may be formed of highly durable and chemically resistant metals or plastics; be of relatively large bore to provide large volume carrying capacity of fluid; and be of rigid and inflexible construction able to withstand relatively high hydraulic pressure and high fluid velocity rates. Clearly, many different and divergent embodiments for the conduit are intended and expected; all of these are deemed to be within the scope of the present invention.

B. The Modulator unit

The second, essential component part of the present receiving system is a flow-through modulator unit having at least one fluid-modulating element, a flow inlet, and a flow outlet. The modulator unit illustrated by FIG. 1 in schematic form is positioned external to the source of fluid matter; and is in closed, fluid flow communication with the remote open end of the conduit such that all fluid matter conveyed from the source by the conduit flows into contact with and is acted upon by the fluid-modulating element of the unit to yield a resulting fluid product. Thus, there are two characteristics and functions required of the modulator unit at a minimum: first, that the modulator unit lie in flow-through fluid communication with the source such that the fluid matter conveyed by the conduit also flows into and subsequently flows out of the modulator unit in a generally uninterrupted, closed flow condition. Second, that fluid matter entering the modulator unit flows into contact with and be acted upon at least one fluid-modulating element whereby at least one identifiable property of the fluid matter becomes acted upon by the fluid-modulating element to yield a resulting fluid product. This latter function and property of the modulator unit is a unusual feature and thus deserves special descriptive attention and detail.

The Fluid-Modulating Element

The nature, format, and construction of the fluid-modulating element is intended and expected to be as diverse as the prospective applications and usages for the receiving system as a whole. The fluid-modulating element may be constructed as a single article of manufacture; or, alternatively, comprise a plurality of different articles and apparatus in combination. The action and effect of the fluid-modulating element upon the fluid matter may be gradual or rapid; chemical or physical; subtle or drastic; immediate or delayed; and substantive or trivial.

There are several purposes, results, and consequences characteristic of and associated with the diverse embodiments of the fluid-modulating element. These include: First, the modulating element must make at least physical contact (with or without concurrent chemical contact) with the fluid matter passing through the unit; accordingly, it is demanded that the modulating element lie in or be disposed in position for at least physical continuity and contact with the flow of fluid matter as it passes through the modulator unit. Second, while the modulating element may to some measurable degree retard or reduce the velocity and rate at which the fluid matter passes through the modulator unit, there can be no severe obstruction or effective interruption of fluid flow as such causing substantial or complete blockage of fluid flow through the modulator unit; the demand for fluid flow communication in a substantially unobstructed and meaningfully unhindered manner must continue despite the presence and function of the fluid-modulating element. Third, recognizing that the fluid-modulating element must exist as a discrete entity or moiety within the totality of the modulator unit (but may be comprised of two or more operative parts or constituents), it is highly desirable that the fluid-modulating element provide and maintain the closed integrity of the receiving system in a manner that the ambient environment can not pass through the entirety of the fluid-modulating element; and thus the ambient environment can not disrupt the closed fluid flow communication between the modulation unit, the conduit, and the source of fluid matter at any time. This optional attribute is particularly desirable and important in view of the replaceable nature of the receiver component which ultimately receives and collects the resulting fluid product after it passes out of the modulator unit. Thus, in these preferred embodiments, even when the receiver is removed from the system, one or more constituent parts of the fluid-modulating element situated within the modulator unit—optionally but desirably—provide a barrier function; and prevent the ambient environment from entering the system whether or not the replaceable receiver is then in proper position for fluid flow communication. Fourth, as a result of the contact between the fluid matter entering the modulator unit and the fluid-modulating element, at least one identifiable property (be it physical, chemical, or otherwise) must be acted upon—but not necessarily be altered by—the fluid-modulating element to yield a resulting fluid product. Thus, the requirement for the fluid-modulating element is only for contact and action upon the fluid matter; there is no demand and no requirement that the identifiable property of the fluid matter being acted upon consequently be altered, modified, changed, or influenced in any manner, mode, or degree. It should be noted, however, that in many instances and applications, a chemical reactive contact and result in addition to the minimal physical contact is desirable; and a drastic alteration rather than no meaningful modification or change at all, is useful. Under these alternative circumstances, meaningful changes and substantive modifications in physical and chemical state will occur. Nevertheless, it will be appreciated that these instances are solely optional as such; and that there is no insistance or necessity that a consequential change in one or more properties of the fluid matter result from the action by the fluid-modulating element upon at least one identifiable property of the fluid matter.

Exemplifying and merely illustrating the range and variety of favored constructions for the fluid-modulating element of the modulator unit are those constructions described subsequently herein. Of these, the porous matrix layer or filter is most preferred. Such articles are conventionally known and commercially available as porous membrane filters composed of varying compositions such as cellulose, nitrocellulose, nitroacetate, metals, clays, crystals, as well as many more complex organic and inorganic substances. Such porous membranes provide a wide range of pore sizes, total pore volume or void volume capacity, and diverse surface characteristics. Alternative formulations of porous filters also include amorphous porous glass filters and silicates, refractory ceramic fibers and mineral mixtures, and plastics constructed as various nettings, weaves, and textiles; as well as other cloths, fabrics, and constructions of porous nature. Often, it is desireable to employ a plurality of these porous filters or matrix layers in series as a stack of variable thickness; and to intermix different compositions of materials within each of the individual porous matrix layers so as to provide a range of different properties for each layer in the stack of filters. Of these porous matrix layers and filter materials in individual format or in multi-layer combinations are conventionally known and used; all of these are therefore deemed to be within the scope and construction for the fluid-modulating element.

Another favored construction and format for the fluid-modulating element is the conventionally known, unidirectional flow valve which allows a fluid to pass through while Prohibiting backflow of fluid in the opposite direction. Such unidirectional flow valves, commonly called "check" valves, are conventionally available in varying constructions and formats. Most preferred is the cylindrical housing whose internal diameter contains a plurality of individual blades or leaves which overlap one another, each blade or leaf being rotably joined to the interior walls of the cylinder housing. Thus, fluid entering the cylinder housing pushes and rotates the blades into a flattened position thereby allowing the fluid to pass through the cylinder, while any attempted backflow of fluid in the opposite direction raises the individual leaves into the flow pathway to form an integral wall of interlocking leaves which effectively prevents fluid movement in the return direction. Clearly, many other constructions and formats of such unidirectional flow valves are conventionally known and commercially available. Moreover, it is most desireable that the unidirectional flow valve be employed in combination with the porous matrix layer or filter material. It is deemed that a variety of far more complicated and elaborate constructions for a fluid-modulating element can and will be prepared to meet specific use circumstances and applications. Accordingly, regardless of the complexity of design or the nature of the materials used for construction and without regard to whether the modulating element is a single, discrete article or composed of a plurality of different constituent parts, so long as the essential functions and purposes as delineated above are fulfilled and achieved, that particular design and construction lies within the scope of the present invention.

Optional Chemical Constituents For Inclusion Within The Fluid-Modulating Elements While the minimal demand and requirement for the fluid-modulating element of the modulator unit is that physical contact be made with the flowing fluid matter and that at least one identifying property of the fluid matter be acted upon (but not necessarily altered) by the fluid-modulating element to yield a resulting fluid product, it is optionally available and often highly desireable that one or more chemically active substances be added to and combined with the minimal constituents comprising the fluid-modulating elements. Although the present receiving system as a whole permits the user to position chemically active substances or articles at any location within the closed, flow-through system from the conduit to the replaceable receiver,, the modulator unit generally and the fluid-modulating element in particular are highly favored locations for the addition/inclusion of chemical reagents and reactants.

Clearly, the range and diversity of chemical compositions suitable for use as chemical reactants and reagents is huge; and includes all of the conventionally known organic and inorganic compositions of matter as well as their attributed properties, characteristics, and reactions as conventionally known and recognized in the scientific literature. The variety of chemical reagents and reactants therefore includes: initiators; activators; functional and radical groups and moieties; the conventionally known acids and bases; as well as all the classes of chemical compounds generally known and understood. The kinds and categories of compositions would therefore include catalysts; enzymes, substrates, and cofactors; specific binding entities such as antibodies and antigens; as well as non-specific cross-linking substances such as monomers, homopolymers, and copolymers. The range of desired results and consequences caused by the presence of such chemical reagents and reactants could thus provide germicidal properties; toxic reduction properties; inactivation and/or neutralization; and biological or pharmacological potency loss—among others. Clearly, therefore, the choice of which chemical substance to include as an optional constituent of the fluid-modulating element thus will be controlled and decided by the user and by the desired result. This is clearly shown by an illustrative example.

For descriptive and illustrative purposes alone, a favored embodiment for the fluid-modulating element is employed - a porous matrix layer or filter membrane. Such porous matrices have a plurality of external and internal surfaces through the thickness of the matrix layer; and provide a far greater surface area for deposition and attachment of one or more chemical compositions for subsequent reactive contact with the fluid matter passing therethrough. The choices of which chemical substances to employ become dictated by the intended application for the receiving system as a whole. For example, with in vivo applications of the receiving system for drainage of fluid matter from a surgical wound or incision, it is highly desireable to deposit a broad germicidal agent such as a phenolic compound or an iodine containing substance directly onto the external and internal surfaces of the porous matrix layer. Moreover, if the drainage fluid from the surgical wound or incision is suspected of carrying infectious bacteria, a variety of selective anti-microbial agents can be disposed upon the external and internal surfaces of the porous membrane using conventionally known methods. Alternatively, the user may include a porous material as an additional layer or membrane directly above or below the porous matrix layer initially present; and in this manner compel a flow-through of the fluid matter through the chemical reagents and reactants as a separate and individual occurrence in addition to the flow-through the primary porous membrane layer.

It will be recognized and appreciated therefore that a host of chemical reagents and reactants may be optionally introduced into the flow-through system as discrete compositions and/or articles which come into individual reactive contact with the fluid matter as an addition to the passage of the fluid matter through the fluid-modulating element as such. Under these alternative flow circumstances, the chemical substances may take physical form within the system as capsules, discrete layers or particles; or as integral articles of manufacture which can be periodically replenished if desired. These diverse chemical formats may be individually supported by an open netting or other porous supports—the nature, format, and construction of these supporting materials being of no consequence or importance so long as the free flow of fluid matter remains substantially unobstructed and unhindered.

C. The Replaceable Receiver

The third and final essential component of the system which is the present invention is a replaceable receiver positioned in closed, fluid-flow communication with the modulator unit for receipt and collection of the resulting fluid product. The receiver is a closed container or receptacle of determinable dimensions and configuration; and has an internal volume which is not less than partially filled with at least one superabsorbent fibrous material comprising fluid-absorbing fibers able to absorb at least 15 times their own weight of liquid. Accordingly, such resulting fluid product as flows from the modulator unit into the receiver is at least partially, if not completely, absorbed by the superabsorbent fibrous material.

The Physical Format And Construction Of The Replaceable Receiver

It will be recognized that the format, construction,, materials, dimensions, configuration, and total volume or capacity for the receiver will vary with the intended mode of use or application. Typically for in vivo applications, the receiver will be of minimal size and volume, portable, and be constructed of flexible materials which can be subjected to heat or steam sterilization without deteriorating. Thus, when formed as a urinary catheter system or as an ileostomy/colostomy receiving system, the receiver is intended to be frequently replaced and is expected to be portable and small enough to be carried comfortably on one's person. Alternatively, in industrial applications for the receipt and collection of waste,, hazardous, and/or toxic fluid matter, the replaceable receiver will typically take form as chemically resistant 55 gallon drums or large volume holding tanks which demand the use of mechanical equipment for removal. Accordingly, neither the dimensions, volume capacity, construction materials, or manner of construction for the receiver are of any importance or meaning whatsoever.

It is intended and envisioned, however, that the receiver be replaceable on an ongoing basis as the needs or desires of the user dictate. The present invention therefore expects that: because the receiver must be positioned in closed, fluid-flow communication with the modulator unit for receipt and collection of resulting fluid product; and also because the receiver is expected to be replaced periodically by necessity or desire; that the design and construction of the receiver be such that it comprise means (such as connectors) for achieving and disrupting fluid-flow communication at will with the remainder of the system. It is also highly desireable that the receiver be constructed with a self-sealing closure and/or a one-way flow valve which effectively seals the internal contents of the receiver during those time periods when the receiver is not directly positioned in fluid-flow communication with the modulator unit. This sealing closure, however, is an optional but highly desireable feature of the receiver construction.

The Superabsorbent Fibrous Material

Figure 2:
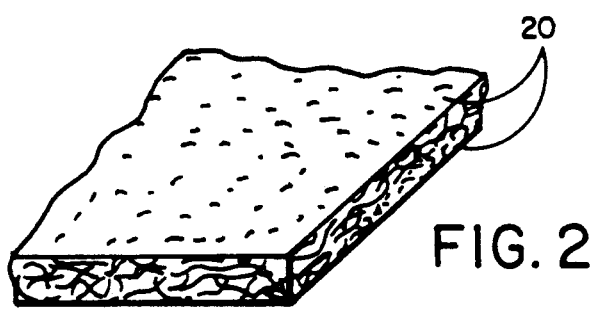
FIG. 2 is an illustration of the preferred construction of superabsorbent fibrous material disposed within the receiver.
Figure 3:
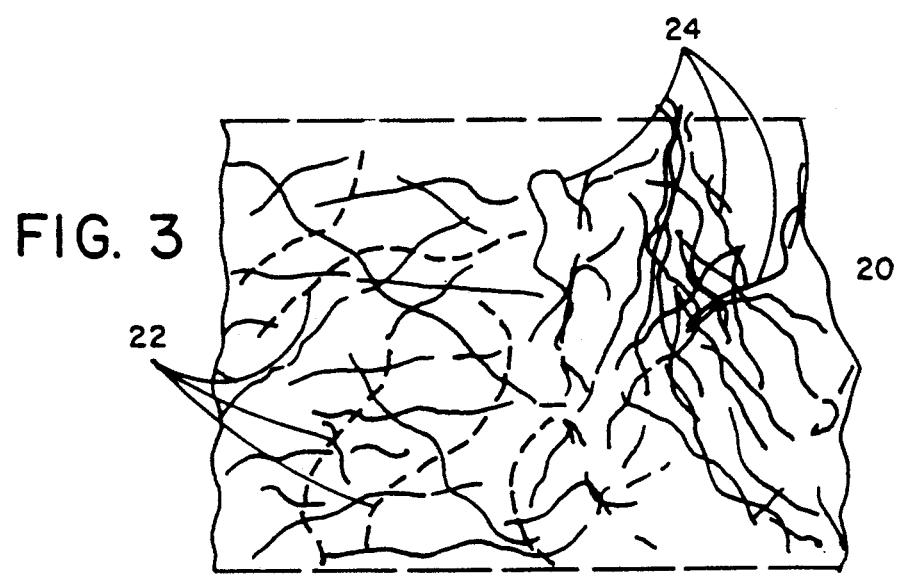
FIG. 3 is a magnified cross-sectional view detailing the construction of superabsorbent fibrous material of FIG. 2.

The preferred superabsorbent fibrous material filling at least part of the receiver's internal volume is illustrated by FIGS. 2 and 3 respectively. FIG. 2 shows a perspective view of the superabsorbent fibrous material as a sheet construction. As illustrated, the fibrous material is most desirably formed as a superabsorbent sheet-like layer 20 comprising fluid-absorbing fibers able to absorb at least 15 times their own weight of liquid. The preferred form and embodiment of these superabsorbent fibers is as a non-woven absorbent batt composed of a substantially uniform array of superabsorbent fibers 22 (able to absorb not less than 15 times their own weight of liquid) and support fibers 24. While the primary function of the superabsorbent fibers 22 is to absorb high volumes of liquid, the support fibers 24 interlock with the superabsorbent fibers 22 to provide strength and stability for the superabsorbent fibrous batt both before and after it is saturated by liquid. The support fibers 24 also provide good absorbent and adsorbent qualities and offer good resiliency when either in wet or dry states. In general, the superabsorbent fibers 22 typically comprise between 5-50% of the total fiber content for the non-woven absorbent batt.

It will be noted and appreciated that the preferred sheet-like layer construction for the superabsorbent fibrous material as described herein is part of the subject matter described and claimed within copending patent application of Conrad A. D'Elia and John D. Hogan, entitled "Superabsorbent Non-woven Fibrous Material," the text of which is expressly incorporated by reference herein. In addition, the most preferred composition and blend of fiber materials to be described subsequently also comprises a major part of the above identified, copending patent application. Preferably, the superabsorbent fibers employed in the non-woven absorbent batt within the construction is a fiber formed from a blend of heterocyclic carbonate and a copolymer of maleic anhydride and isobutylene, as described in U.S. Pat. Nos. 4,616,063; 4,705,773; 4,731,067; 4,743,244; 4,788,237; and 4,813,945 respectively—the text of which are also individually incorporated by reference herein for their disclosures.

For optimal absorptive function by the non-woven absorbent batt, the superabsorbent fibers are mixed with support fibers, preferably using several deniers of polyester. A variety of other materials and compositions may also be used for the support fibers themselves. These include: rayon, cotton, polypropylene, nylon, and polyethylene. These support fibers, regardless of specific composition or materials, should interlock with the superabsorbent fibers, preferably in a non-woven manner. In addition, although a great range of percentage content for the support fibers may be utilized, the percentage ratio of support fibers typically comprises 50-95% of the total fiber content for the absorbent batt.

The fluid absorption characteristics and volume capacity of the superabsorbent fibrous material (as noted by the disclosure within copending application of Messers. D'Elia and Hogan) are determined by many factors including superabsorbent fiber content, the composition of the support fiber material, batt density, and padding size. It is recognized also that the horizontal and vertical water retention properties of the absorbent fibrous layer will vary markedly with alterations in the nature and percentage content of superabsorbent fiber versus support fiber, the denier, the fabric weight, and the composition of the support fiber. If and when the preferred blend of heterocyclic carbonate and copolymer of maleic anhydride and isobutylene is employed, polyester is the most desirable material for use as the support fiber for combination with the superabsorbent fiber. Polyester polymers contribute excellent absorbency properties adjunct and complementary to those of the absorbent fibers themselves when present in sufficient density. Moreover, whenever finer denier of support polyester fibers is employed, the overall fluid retention capacity is clearly increased such that various embodiments of the preferred materials are able to absorb 60 fold and sometimes up to 100 fold their product weight of water or other fluid.

To illustrate and to understand how the preferred construction for the superabsorbent fibrous material works, FIG. 3 illustrates a cross-sectional view of the construct in greater detail. The support fibers 24 are shown as solid lines while the superabsorbent fibers 22 are provided as dashed lines so that they can be distinguished from one another. In the unused, dry state, both the superabsorption fibers and the support fibers may criss-cross and bend as indicated within FIG. 2. When the absorbent batt absorbs liquid and becomes wet, the superabsorbent fibers 22 can swell to many times their original dry size, up to and including about 100 times their diameter when dry. In addition, the swelling of the superabsorbent fibers upon wetting exerts force upon the support fibers 24 in the batt and stiffens them. Accordingly, in many instances, the absorbent batt forces fibers which are only loosely crossed and meshed in the dry state to tightly lock and support each other in the wetted fluid absorbent state. This mechanism is believed to account in part at least for the superabsorption capability of the fibrous layer to retain its physical integrity even when holding many times its weight in liquid.

It should be noted and appreciated also that a wide range and diversity of other compounds and chemical compositions are believed to be conventionally available and known as substitutes and replacements for the preferred composition for superabsorbent fibers as described above. The range, variety, and diversity of such superabsorbent materials and compositions is described within the following publications: water absorbing acrylic copolymer compositions prepared from acrylic acid monomers and hydrophilic unsaturated carbonate monomers as described within Japanese Patent Publication No. 63242344 (881017); the water absorptive composites of impregnated natural or synthetic fibers with modified acrylic acid described within European Patent Publication No. 290814 (881117); water-swellable cross-linked polymers of vinyl-saccharide monomer as described by European Patent Publication No. 283090 (880921); a superabsorbent for blood and proteinaceous fluid comprising insoluble ionic macromolecular material in acidic form as described within French Patent No. 2602985 (880226); water absorptive fibrous composite materials containing polymerized partially neutralized acrylic acid which is cross-linked using glycidyl ether compounds as described by European Patent Publication No. 232121 (870812); water-absorbing polymer compounds prepared by polymerization of acrylic acid (alkali metal) salts in the presence of alpha-olefins and carboxylic acids as described within Japanese Patent Publication No. 62053310 (870309); and a fluid absorbing composition comprising water soluble carboxylic copolyelectrolyte cross-linked with di- or polyfunctional aziridine as described within U.S. Pat. No. 4,645,789. It will be recognized and appreciated that the provided listing is merely illustrative and clearly non-exhaustive in its coverage. Many other liquid absorbing materials able to be manufactured and to provide a superabsorbent capability—that is, able to absorb at least 15 times its own weight in liquid—are clearly available and commercially sold today. All such conventionally known chemical compositions, manufacturers, and superabsorbent fibrous materials are deemed to be within the scope of the present invention.

Chemical Agents Which May Be Optionally Combined With The Superabsorbent Fibrous Material A variety of diverse chemical agents may be optionally combined with the superabsorbent fibrous material in the receiver of the present system. The chemical agents desirably include, but clearly are not limited to, the following: chemical initiators, chemical activators, and catalysts; neutralizing agents, buffers, and salts; germicidal agents including static, cidal, and other antimicrobials of varying ranges and properties; chelating agents and other complex forming reactants; enzymes, cofactors, and enzyme substrates; specific binding agents such as antibodies and antigens; agglutinizing agents and flocculating agents; monomers, copolymers, and homopolymers with or without specific cross-linking agents; various oxidizing agents and reducing agents; coupling agents, decoupling agents, and carriers for conjugate formation.

It will be recognized by the range and diversity of chemical reagents and/or reactants optionally present with the superabsorbent fibrous material comprising the receiver that an enormous diversity of chemical reactions and chemical consequences are intended. It will be understood, however, that despite the diversity of chemical compositions employed, the variety of chemical reactions envisioned possible, and the range of reaction products yielded, that all of these employ solely conventional chemistry and chemical reactions well described and commonly understood by persons ordinarily skilled in these technical areas. All of these diverse chemical reactants and reagents are thus deemed to be within the scope of the present invention.

II. SOME PREFERRED EMBODIMENTS OF THE PRESENT RECEIVING SYSTEM

To merely illustrate the wide range of formats and constructions available for the essential components comprising the conduit, the modulator unit, and the replaceable receiver of the present invention, four different preferred embodiments will be individually described. It will be expressly understood, however, that these preferred embodiments are merely illustrative examples of the present receiving system as a whole; and are adduced here to demonstrate some of the various uses and applications for the present invention under both in vivo and non-living conditions.

Moreover, each of the preferred embodiments described in detail hereinafter tangibly exists as and functionally represents an effective answer to and successful resolution of the two fundamental questions which determine and control the value of such systems. It will be expressly noted and appreciated that each preferred embodiment allows one to collect and dispose of the fluid matter without himself coming into meaningful contact with or being detrimentally affected by the fluid matter during the process of collection and disposal; and each preferred embodiment also permits one to effectively collect and dispose of fluid matter without concomitantly influencing, contaminating, or otherwise altering the source from which the fluid matter originates. By providing these capabilities and achievements, the individual preferred embodiments and the receiving system as a whole have differentiated and distinguished themselves from conventional practices and apparatus.

Figure 4:
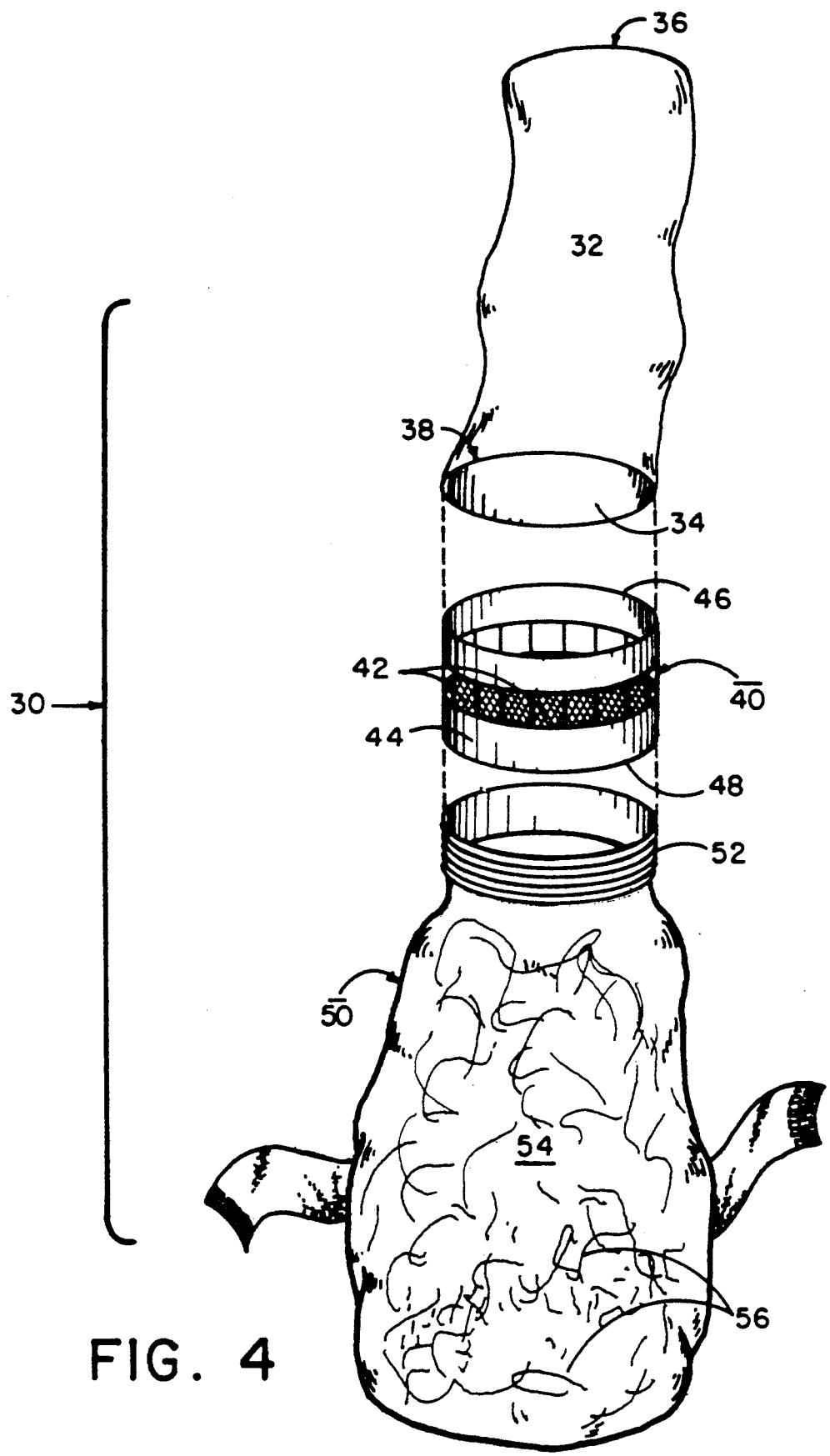
FIG. 4 is an overhead, perspective view of the separated component parts of the drainage fluid receiving system comprising one preferred embodiment of the present invention.
Figure 5:
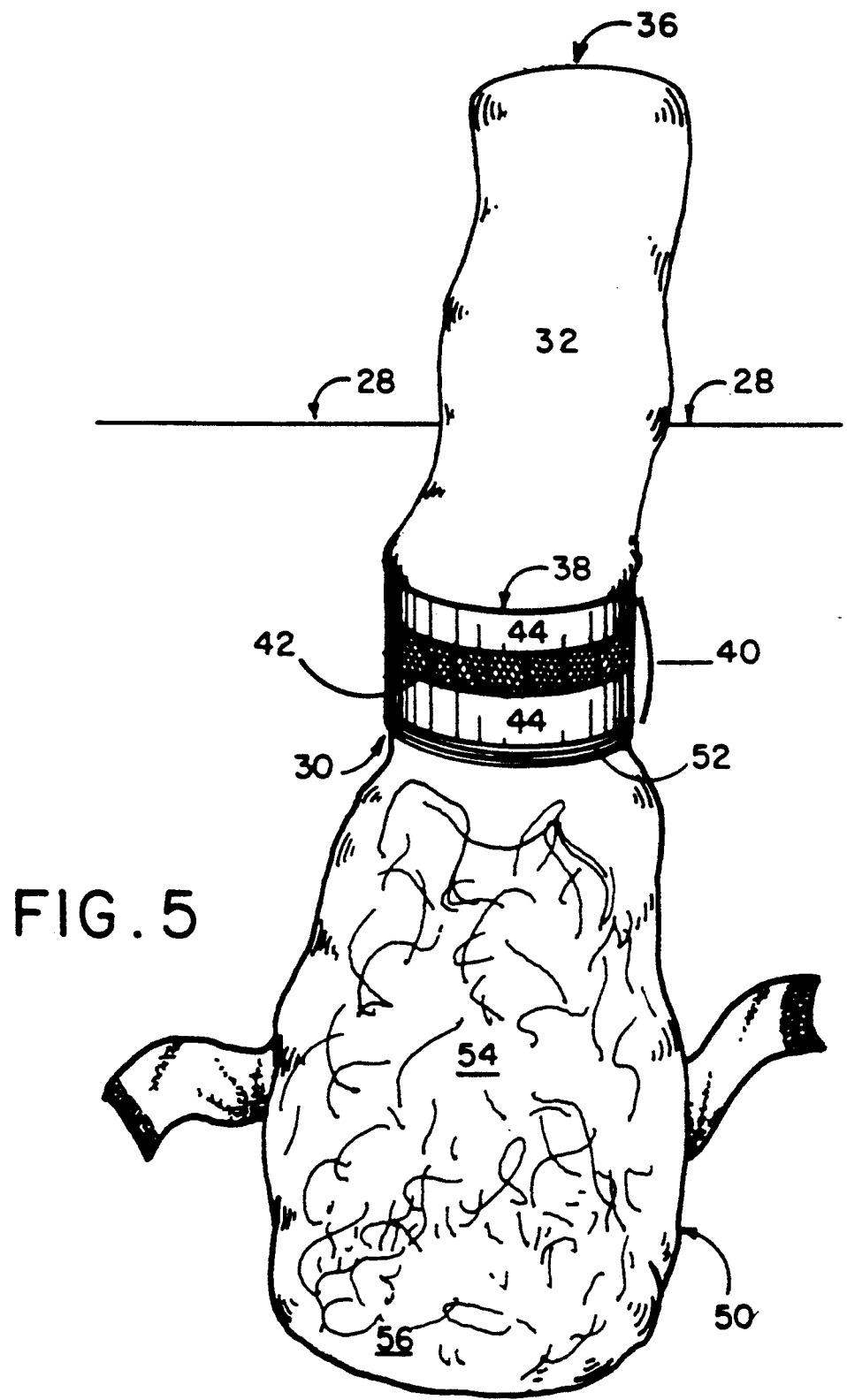
FIG. 5 is another view of the drainage fluid receiving system of FIG. 4 as an assembled in vivo system with regard to a living subject.

A. A System For The Receipt And Collection Of Drainage Fluid From A Surgical Incision In A Living Subject The closed, fluid-modulating receiving system of the present invention employed in vivo for receiving drainage fluid from a surgical incision in a living subject is illustrated by FIGS. 4 and 5. As seen therein, FIG. 4 illustrates the individual component parts when purposefully separated from one another for increased clarity. In comparison, FIG. 5 shows the present receiving system as an integral whole and when performing its intended function with respect to a living subject. Accordingly, FIG. 4 will be recognized as being an artificial separation for purposes of easier understanding and description while the system illustrated within FIG. 5 illustrates the assembled drainage fluid receiving system in proper position and in fluid communication with the internal tissues of a living subject.

It will be recognized that the typical setting and intended usage for the drainage fluid receiving system of FIGS. 4 and 5 is after a wound or surgical incision has been made in the body of a living subject; and the surgeon or physician has made a medical decision to insert a drain in the wound or incision for an indefinite period of time in order that any fluid which might accumulate around the open wound be removed rather than accumulate at that anatomical site. Typical instances of use would be for draining pleural fluids from a diseased or collapsed lung and for draining abdominal (ascites) fluid. Accordingly, a receiving system 30 has been inserted into the surgical incision or wound 28 as appears within FIG. 5. The receiving system 30 comprises: a conduit formed as a drain 32 for draining fluids from a surgical incision in the body of a living subject; a discrete modulator unit formed as a flow-through protective cap 40 which is in fluid flow communication with the drain 32; and a replaceable receiver in the form of a receptacle 50 which is able to be placed in closed fluid flow communication with the drain 32 via the protective cap 40.

The drain 32 is typically a flexible conduit having a closed elongated body of determinable dimensions and a tube-like configuration, an internal lumen 34 for the flow of discharged fluid from the incision or wound, and two discrete open ends 36, 38. The internalized end 36 is positioned within the body of the living subject while the other open end 38 extends externally from the body of the living subject.

The protective cap 40, serving as the modulator unit for the system, is disposed at the external open end 38 of the drain 32 and lies in closed, fluid-flow communication with the internalized open end 36 within the body of the living subject. The protective cap 40 comprises a porous matrix layer 42 and a connector channel 44. In this embodiment, the porous matrix layer 42 is the fluid-modulating element of the modulator unit.

The porous matrix layer 42 occludes the entirety of the external open end 38 of the drain 32 from the ambient environment and thus is typically positioned adjacent to the external open end 38 itself. The porous matrix layer 42 has a plurality of external and internal matrix surfaces such that drainage fluid conveyed by the drain 32 from the surgical incision in the body of the living subject can pass through the porous matrix layer as a resulting drainage fluid product while the ambient environment can not pass through the porous matrix layer in the opposite direction.

As appears in FIGS. 4 and 5, the porous matrix layer 42 lies desirably in the middle of the connector channel 44 which desirably has threaded ends 46, 48 (or some other means of connection) for direct junction with the drain 32 and receptacle in a fluid-tight manner. While it is highly desirable for the connector channel 44 to provide threaded ends for purposes of forming a fluid-tight flow-through protective cap 40, any connector means which achieves fluid flow communication between the porous matrix layer 42 and the drain 32 is suitable for use.

Lastly, the receptacle 50 serving as the replaceable receiver of the system appears as a bottle-shaped article of determinable dimensions and volume. The receptacle 50 serves as the container means for receiving and collecting the resulting drainage fluid product as it is discharged from the porous matrix layer 42. As seen within FIGS. 4 and 5, the top of the bottle-shaped receptacle 50 is preferrably composed of a flexible rubber or plastic substance and formed in part as a series of expandable and compressible ribs 52 and the collection container 54. The expandable and compressible ribs 52 are in fluid flow communication with the porous cap 40 and are preferably screw threaded in order to join directly with the threaded end 48 of the connector channel 44. The expandable and compressible ribs 52 also permit a person to pull or push the receptacle 50 and thus provide a pumping action if necessary or desired to increase the fluid flow rate from the protective cap into the receptable proper.

The internal volume of the receptacle 50 is at least partially filled with a superabsorbent fibrous material 56 able to absorb at least 15 times its own weight of liquid, and preferably is able to absorb between 60-100 times its own weight of liquid. Thus, such resulting drainage fluid product as flows into the internal volume of the receptacle 50 is at least partially and most often entirely absorbed by the superabsorbent fibrous material 56.

In this drainage fluid receiving system 30, it is expected that the drainage fluid itself will comprise blood, lymph fluid mucous, ascites fluid, peritoneal fluids, chest fluids, and the like—all of which are liquids produced by the body of the living subject; as well as various solid, cellular, and/or particulate matter from the tissues and organs of the living subject. It will be recognized and appreciated, therefore, that the modulating unit constructed as the protective cap 40 provides a fluid-modulating element in the form of the porous matrix layer 42 which acts upon the drainage fluid as it passes from the drain 32 into the receptacle 50. The porous matrix layer 42 having the plurality of external and internal surfaces and being porous allows the drainage fluid to pass through while preventing the ambient environment from passing in return through the protective cap into the drain and subsequently into the surgical incision or wound. The porous matrix layer therefore prevents and reduces the risk of post-surgical infections and complications by preventing the ambient environment from making direct entry into the incision or wound via the drain, as customarily occurs in conventional practice.

Similarly, the receptacle 50, being in close fluid flow communication with the drain 32 via the protective cap 40, achieves a closed receipt and collection of drainage fluid; and absorbs the resulting drainage fluid product as it is received by the presence and effect of the superabsorbent fibrous material 56. In addition, in view of the nature and source of the resulting drainage fluid product itself, it is highly desirable that at least one germicidal agent be present within the internal volume of the receptacle 50 in order to diminish or eliminate the potential infectious nature of the fluid itself. Thus, typically, the addition of a phenolic composition or an iodine containing germicidal agent to the superabsorbent fibrous material in advance of using the receptacle or the receiving system provides highly desirable benefits.

The receptacle 50, being replaceable at will or on demand, may be removed and substituted by another similarly constructed receiver as needed or required. It will be appreciated that during the limited time period during which the substitution of receptacles is made by a competent technician or nurse, that the drain 32 is itself completely protected from the ambient environment by the presence and effectiveness of the porous matrix layer 42 within the protective cap 40. Consequently, replacement of the receptacle 50 may be made without fear of accidentally contaminating the drain 32 or consequently affecting the surgical wound or incision itself within the body of the living subject. If desired also, a self-sealing protective closure optionally may be inserted at the protective cap and/or the receptacle 50 to further ensure the prevention of accidental contaminants or infections for the living subject. In this manner, one may also optionally seal the system to avoid changes in pressure (such as for a collapsed lung) when changing and/or replacing the receptacle.

Finally, it will be recognized and appreciated that this drainage fluid receiving system provides for and successfully performs the two necessary and fundamental goals. First, this drainage fluid receiving system allows for the collection and disposal of drainage fluid without any person coming into meaningful contact with or becoming detrimentally affected by the drainage fluid. Second, this drainage fluid receiving system concomitantly permits the effective collection and disposal of drainage fluid without influencing, contaminating, or seriously altering the medical condition and prognosis of the particular patient from whom the drainage fluid was obtained. Thus, despite the relative simplicity of its essential components and organization, this drainage fluid receiving system is uniquely different from its conventionally known counterparts.

B. A System For Receiving Fluid From The urinary Tract in A Living subject

Figure 6:
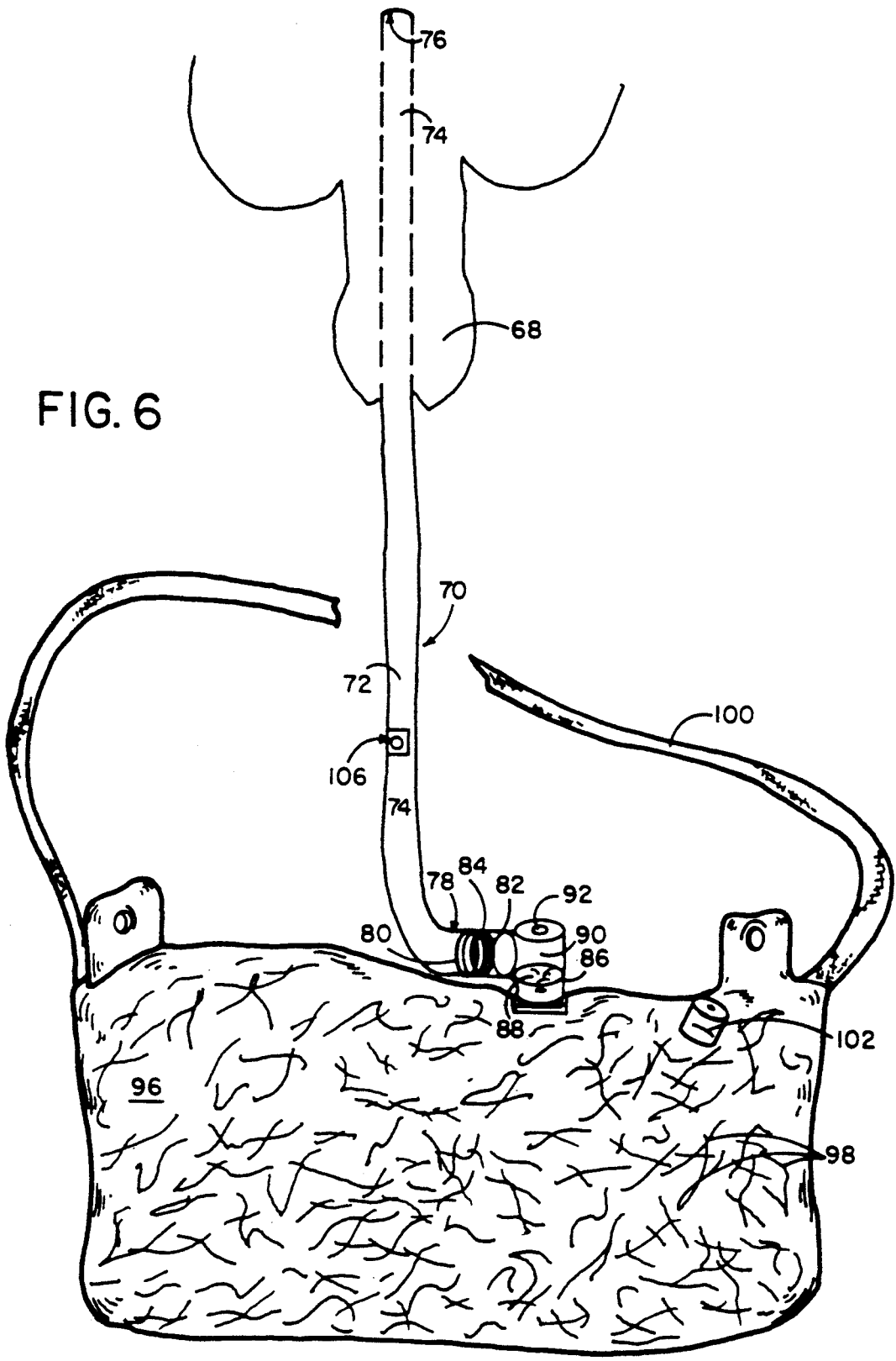
FIG. 6 is a perspective view of a urinary fluid receiving system comprising a second preferred in vivo embodiment of the present invention.

The closed, fluid-modulating receiving system employed in vivo for receiving fluid from the urinary tract in a living subject is illustrated by FIG. 6 as a transparent embodiment for purposes of clarity. It will be recognized that the transparent format for this embodiment is employed for descriptive purposes only; and that the urinary tract receiving system is suitable for incontinence, tumors, and post-surgical use as well as for the particular application of relieving and removing accumulated urinary fluid from the bladder of a male or female living subject without regard to the health of the person.

For descriptive purposes only, a male subject appears within FIG. 6; and the urinary fluid receiving system 70 has been internalized through the penis 68 of the male subject and extended internally to reach the urinary bladder (not shown) in accordance with conventional practice for this purpose. The urinary fluid receiving system 70 thus comprises a conduit formed as a flexible catheter 72 for removing fluid from the urinary tract of a living subject; a discrete modulator unit formed as a one-way, flow-through coupling 80 in fluid flow communication with the catheter; and a replaceable receiver in the form of a collection vessel 96 positioned in closed, fluid flow communication with the coupling and the catheter.

The transparent nature and three-dimensional forms illustrated by FIG. 6 reveal the catheter 72 to be a flexible conduit having an internal lumen 74, an internalized open end 76 lying within the urinary tract of the living subject, and an externalized open end 78 extending externally from the penis of the living subject. The catheter 72, as well as the entirety of the receiving system 70, is preferably presterilized in advance of usage and insertion within the urinary tract.

The coupling 80, serving as the modulator unit of the system, is formed as a one-way, flow-through article disposed at the external open end of the catheter 72 and lies in closed,, fluid flow communication with the internalized open end 76 positioned within the urinary tract. The coupling comprises a connector 82, a porous matrix layer 84, and an optional but highly desirable unidirectional flow valve 86. Alternatively, the coupling may optionally comprise only the porous matrix layer 84 and the connector 82 alone. Either embodiment will function equally well for purposes of the receiving system.

By the position of the coupling 80, the porous matrix layer 82 occludes the entirety of the external open end 78 of the catheter 72 from the ambient environment; and thus functions as a porous barrier protecting the urinary tract of the living subject from accidental contamination or infection. The porous matrix layer 82 has a plurality of external and internal matrix surfaces such that urinary fluid from the living subject can pass through as a resulting urinary fluid product while the ambient environment is prevented from passing through the porous matrix layer. Accordingly, the porous matrix layer 82 serves as the fluid-modulating element; and physically acts upon the liquid state of the urinary fluid to yield a resulting urinary fluid product. If desired, a variety of different chemical substances may optionally be applied as a covering or coating over the external and internal surfaces of the porous matrix layer in order that one or more chemical reactions may also occur. In this manner, a pH sensitive dye reagent may be applied to the porous matrix layer; and the resulting urinary fluid product will then exhibit and demonstrate a specific color reaction to the observer which indicates the acidic or basic PH value of the fluid.

The optional unidirectional flow valve 86 lies within the connector 82 and allows the resulting urinary fluid product discharged from the porous matrix layer 84 to pass through while prohibiting backflow in the opposite direction. The flow valve 86 is thus a "check" valve and functions as an aid within the system 70 to promote a single directional flow of fluid. It will be recognized and appreciated that the unidirectional flow valve 86 may optionally comprise part of the coupling 80 or, in alternative formats, may comprise an integral feature of the collection vessel 90 itself.

In its most preferred construction, the flow valve 86 provides an interlocking series of blades 88, a retention chamber 90, and a sampling port 92. The retention chamber 90 provides for the retention of a small volume of fluid prior to exiting through the blades 88; and the sampling port 92 allows a technician or nurse to insert a syringe or other sampling device for the removal of aliquot volumes of the fluid prior to its flow into the collection vessel 96. All of these features within the unidirectional flow valve 86 are optional; and may be either employed or eliminated at the desire or needs of the user.

The collection vessel 96, serving as the replaceable receiver of the system,, is a flexible container of determinable dimensions and internal volume. The collection vessel 96 is positioned in closed, fluid flow communication with the catheter 72 via the coupling 80 and thus provides the terminus for the system as well as the point of final collection. The collection vessel 96 thus serves as the means for receiving and collecting such resulting urinary fluid product as is provided; and contains at least one superabsorbent fibrous material able to absorb at least 15 times its own weight of liquid. In this manner, such resulting urinary fluid product as flows into the collection vessel is absorbed at least partially, if not entirely, by the superabsorbent fibrous material.

The collection vessel 96 illustrated within FIG. 6 is configured to provide several optional, but highly desirable features. The collection vessel itself appears as a flexible receiver having an optional carrying strap 100 which desirably allows the person to remain completely mobile even while catheterized. In addition, an inlet 102 optionally allows a technician or nurse to introduce volumes of a disinfecting chemical agent such as bleach or a peroxide solution directly into the internal volume of the collection vessel 96. The inlet 102 may also be employed for the introduction of any other chemical reagent or reactant to accommodate the desires or needs of the user.

It will be appreciated also that the collection vessel 96 is a replaceable receiver; and it is intended that periodic replacement of the collection vessel will be made over hours or days. During the time required for replacement of each collection vessel as necessary, it is clear that the porous matrix layer of the coupling, at a minimum, provides a physical barrier and desirable protection for the living subject in that the ambient environment (and all that it contains) is prevented from passing through the system into the urinary tract.

In addition, in view of the conventional practice regarding irrigation of the catheter 72 as a hygienic procedure to avoid and ensure the absence of obstructions or blockages within the catheter 72 or the urinary tract itself, it is optional within the system to provide for a port of entry 106 in the externalized portion of the catheter for this purpose of irrigation. This entry port 106 remains closed/sealed until purposely opened by an attendant to perform the irrigation procedure. In this manner, standard sterile saline or other irrigation liquid will be introduced via the entry port 106 into the lumen of the catheter; act in the customary way to irrigate lumen and urinary tract; and serve to prevent potential obstruction in the catheter. The irrigation fluid introduced into the catheter in this way will flow by gravity through the lumen towards the external open end of the catheter where it will make contact with the porous matrix layer of the coupling. The irrigation fluid will then itself pass through the external and internal surfaces of the porous matrix layer and itself then flow through the coupling and be received and collected subsequently within the collection vessel. The irrigation fluid itself will then also be absorbed in its entirety by the superabsorbent fibrous material contained within the collection vessel.

Finally, it will be noted and acknowledged that this urinary fluid receiving system as a whole accomplishes and capably performs the underlying two fundamental goals necessary for such systems. First, this urinary fluid receiving system achieves the receipt, collection, and disposal of urinary fluid without any person coming into meaningful contact with or becoming detrimentally affected by the urinary fluid. Second this urinary fluid receiving system permits the effective receipt, collection, and disposal of urinary fluid without any risk of influencing, contaminating, or altering the health or medical status of the particular person from which the urinary fluid was obtained. Therefore, despite its superficial similarity to its predecessors, the capabilities and achievements of this urinary fluid receiving system meaningfully distinguish and substantively separate the present system from all others.

C. A System For Receiving Fluid Fecal Matter From A Resected Bowel In A Living Subject A closed, fluid-modulating receiving system employed in vivo for receiving fluid fecal matter from a resected bowel in a living subject is illustrated by FIGS. 7-12 respectively. The fluid fecal matter receiving system comprises: a conduit formed as a bowel retaining ring for retaining the resected end of the bowel in a living subject for conveyance of fluid fecal matter from the living subject, the fecal matter itself being fluid and composed of gaseous, liquid, and solid fecal constituents; a modulator unit formed as a flow-through, variable volume diaphragm chamber 214 for removable juncture to and for fluid communication with the bowel retaining ring; and a receiver in the form of a flexible pouch and surrounding bandage 240 encompassing and in closed fluid flow communication with the variable volume diaphragm chamber and the bowel retaining ring, this flexible pouch/surrounding bandage comprising porous membrane means for releasing such gaseous fecal material as inflows into the flexible pouch into the ambient environment.

Figure 7:
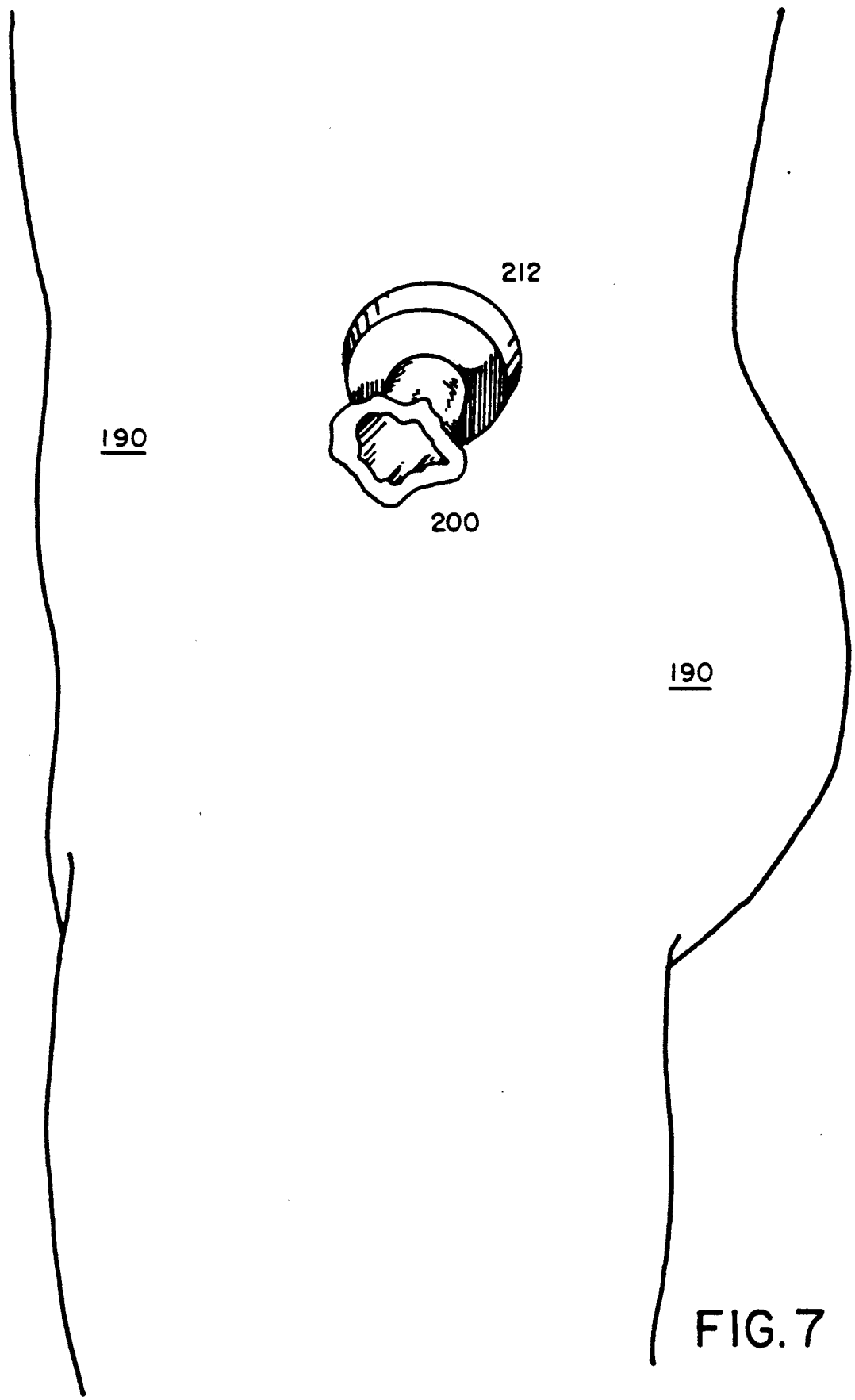
FIG. 7 is a perspective view of a resected bowel end and the first component part of an in vivo fluid fecal matter receiving system comprising a third preferred embodiment of the present invention.
Figure 10:
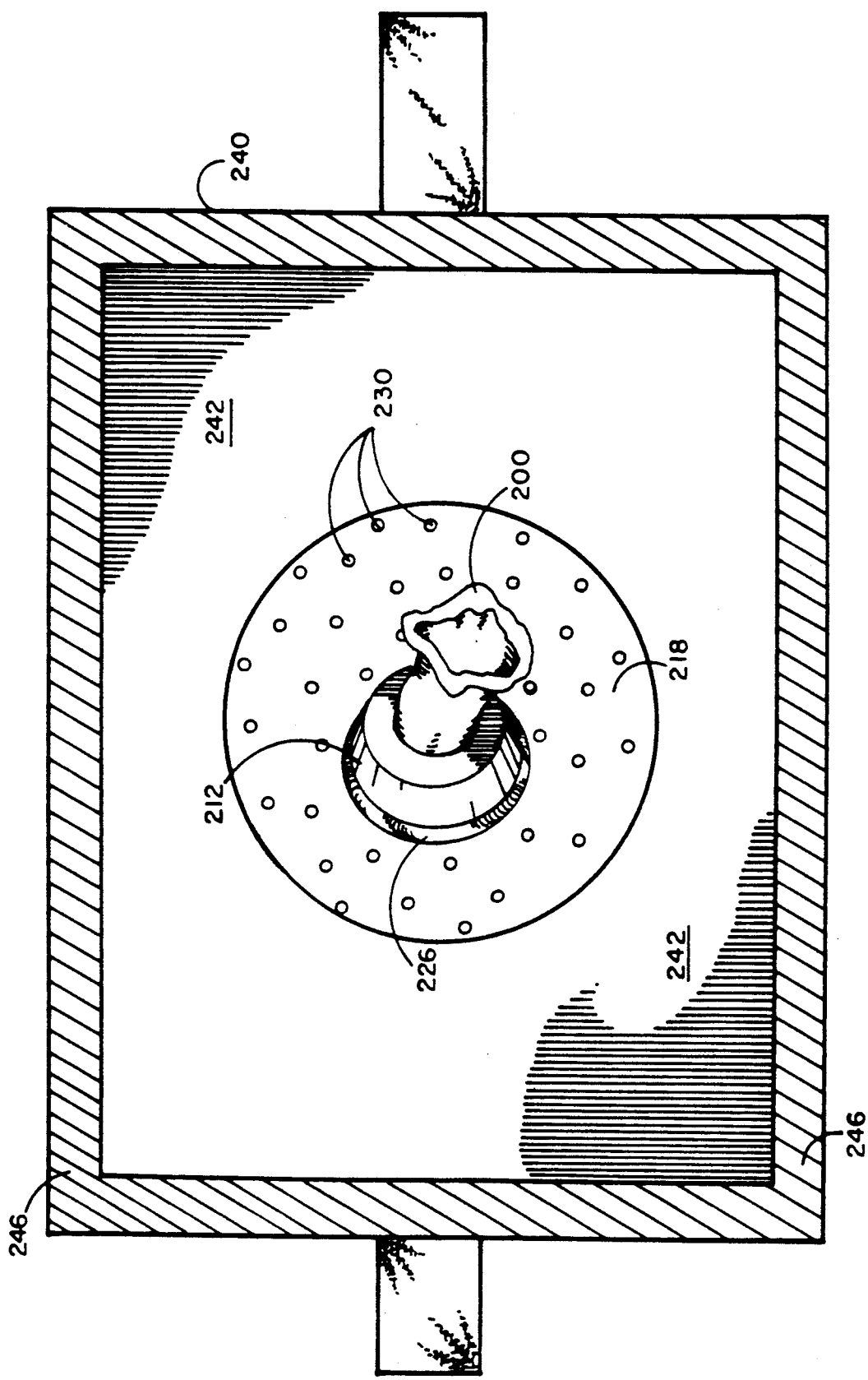
FIG. 10 is a perspective view of the resected bowel end in position with the fluid fecal matter receiving system of FIGS. 7-9.
Figure 11:
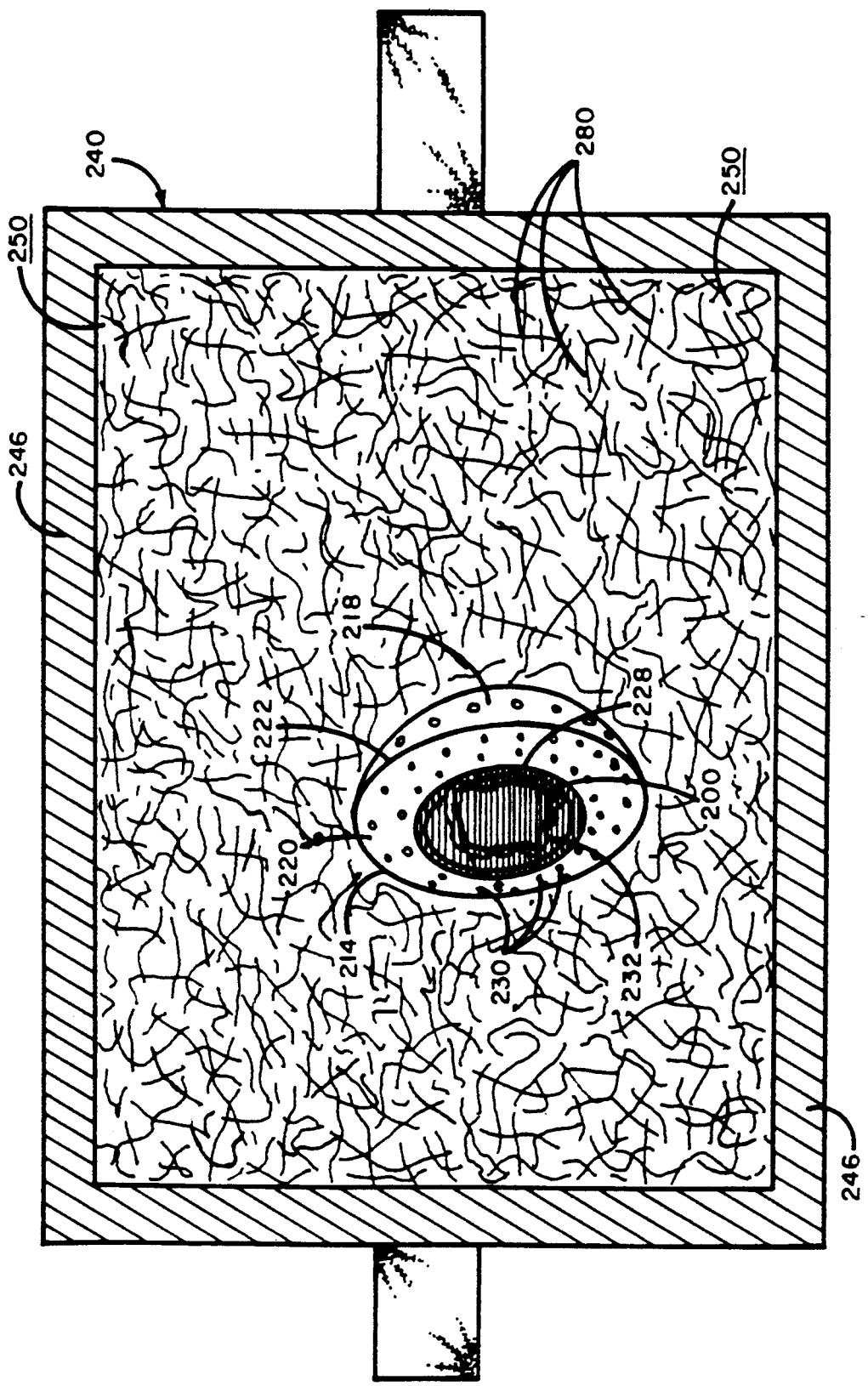
FIG. 11 is an alternative sectional view of the second and third component parts of the fluid fecal matter receiving system of FIGS. 7-10.

As seen within FIGS. 7 and 10, the receiving system 210 is intended for in vivo use with the resected bowel in a living subject after either ileostomy or colostomy. The resected bowel end 200 typically extends externally from the side of the living subject after surgery in order that fluid fecal matter (including gaseous, liquid, and solid fecal materials) pass directly from the internal remainder of the bowel out of the body. Initially, as seen within FIGS. 7 and 10, a bowel retaining ring 212 is positioned around the stroma of the resected bowel end 200 extending externally from the body. The bowel retaining ring 212 encompasses and retains the externalized portion (the stroma) of the resected bowel; and serves also as the point of physical attachment and anchorage for the other component parts of the receiving system. The bowel retaining ring 212 is desirably composed of a soft but resilient substance; and is preferably a substance which offers Some useful degree of elasticity and flexibility while positioned on the resected bowel end so that the wearer will avoid both discomfort and/or irritation during use. Moreover, the bowel retaining ring can be sterilized either prior to or after use; and may periodically be replaced on an irregular or scheduled time basis.

The bowel retaining ring 212 is unique within this embodiment in that it achieves and provides for the conveyance of fluid fecal material from the living subject by encompassing the external surface of the resected bowel itself. In this instance, the bowel retaining ring 212 functions and serves as a structural connector and link without which the physical passage and transfer of fluid fecal matter would not otherwise occur. Furthermore, because the flow-through modulator unit and the replaceable receiver of this embodiment are in fact joined to the bowel retaining ring while in its intended position, it will The recognized and appreciated that the resected bowel end 200 extending from the living subject is actually inserted into and becomes encompassed by the remainder of the receiving system itself. This is clearly illustrated via FIGS. 10, 11, and 12 collectively.

The variable volume diaphragm chamber 214 serving as the discrete, flow-through modulator unit of the system, is constructed for removable juncture to and for closed fluid communication with the bowel retaining ring 212 and the bowel end 200. The diaphragm chamber 214 comprises an expandable and compressible housing 216; means within the housing for separating solid fecal material from liquid and gaseous fecal material in the conveyed fluid fecal matter; and means for removing the separated liquid and gaseous fecal material from the diaphragm chamber as a resulting fecal fluid product. Detailed views of the variable volume diaphragm chamber 214 are illustrated by FIGS. 8A and 8B respectively.

Figure 8B:
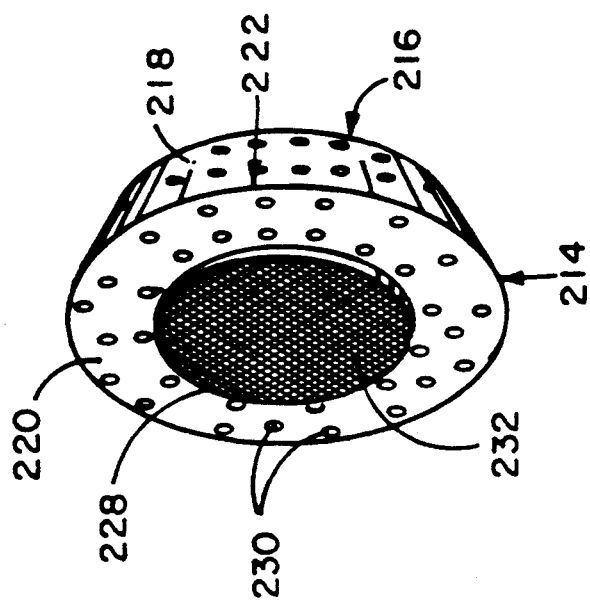
FIGS. 8A and 8B are alternate perspective views of the second component part of the in vivo fluid fecal matter receiving system of FIG. 7.
Figure 8A:
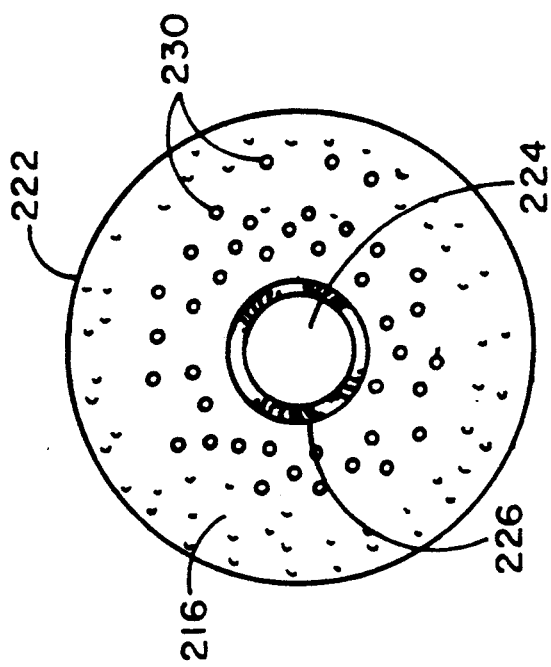

FIG. 8A shows an overhead frontal view of the diaphragm chamber while FIG. 8B shows a perspective, rear view of the diaphragm chamber. The housing 216 is an expandable and compressible construction formed by a front plate 218 and a back plate 220. The front and back plates 218, 220 are preferably formed of a flexible metal or resilient plastic; and are desirably joined together along a common edge 222. The front plate 218 has a small diameter inlet 224 which is desirably encircled and bounded by an elastic, fluid-tight closure 226. The back plate 220 contains a large diameter outlet 228. Positioned within the front plate 218 and the back plate 220 are a plurality of apertures 230.

Within the interior volume of the housing 216 is a large pore netting 232 which, at a minimum, covers the entirety of the outlet 228 and desirably serves as a liner for the entirety of the internal volume of the housing. The netting 232 serves as the separation means within the housing 216 for separating solid fecal material from liquid fecal material and gaseous fecal material constituting the fluid fecal matter conveyed by the resected bowel 200 via the bowel retaining ring 212 into the inlet 224. The netting 232 is desirably formed of the highly elastic material, is flexible and extendable, and retains its tensile strength even while distorted. Moreover, during the separation of solid fecal material, it is expected that the netting 323 will become so enlarged and distorted by the retention of solid fecal material; and that the netting will be caused to extend physically through the outlet 228—all without tearing, fragmenting, or otherwise reducing its effective separation capacity.

Figure 9:
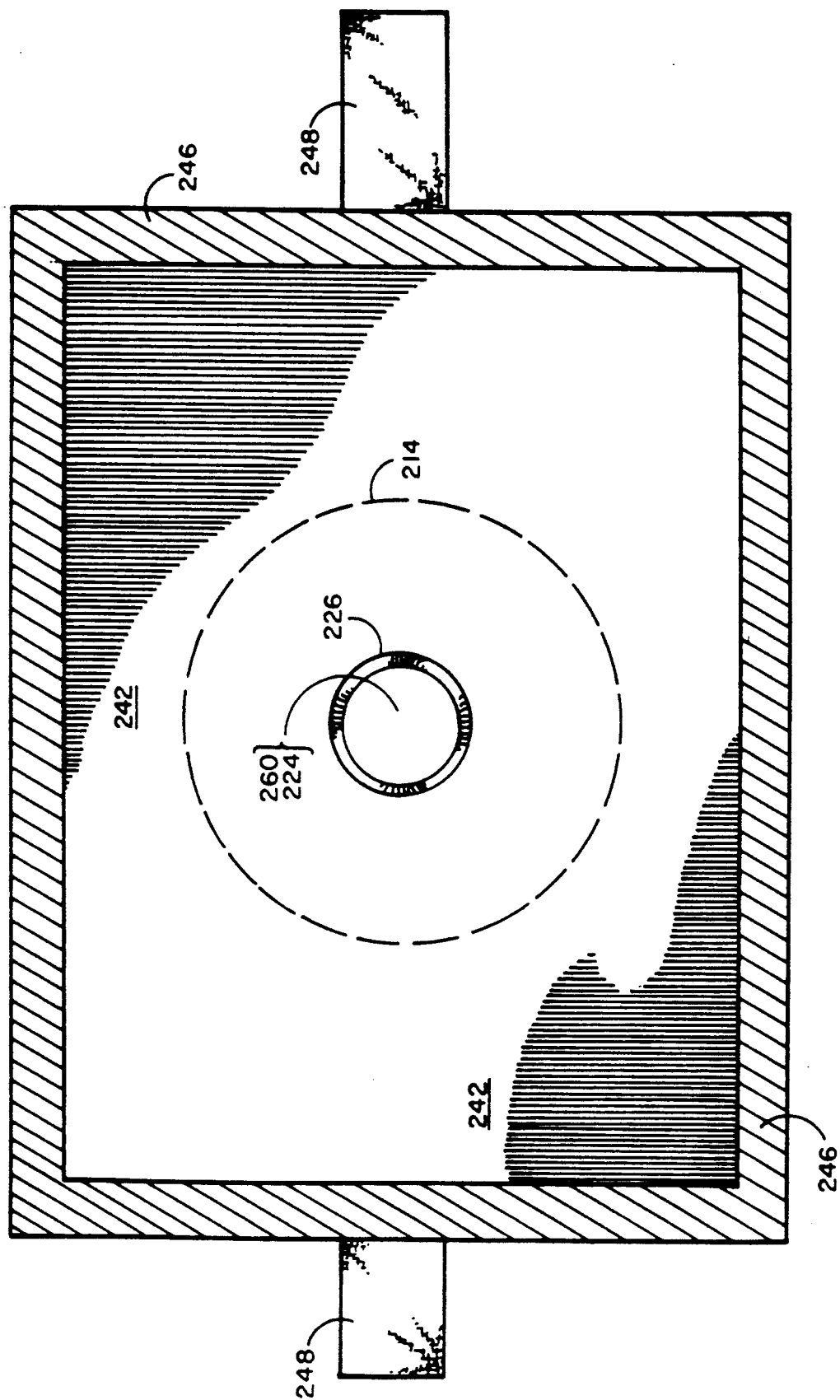
FIG. 9 is a frontal view of the third component part of the in vivo fluid fecal matter receiving system of FIGS. 7-8.

The variable volume diaphragm chamber 214, serving as the flow-through modulator unit of the system, is itself positioned and contained as a discrete entity within a receiver of determinable dimensions and volume constructed desirably in the form of a flexible pouch with surrounding bandage 240. The positioning and placement of the diaphragm chamber 214 within the flexible pouch 240 is illustrated by FIGS. 9, 10, 11, and 12. The flexible pouch 240 is constructed as an expandable/inflatable receiver comprising at least a front wall 242 and a rear wall 244 joined together along a common seam 246 via a fluid-tight seal. A set of body straps 248 are present to enable the living subject to wear the flexible pouch and diaphragm chamber combination as a surrounding bandage with relative ease. Note that the interior volume 250 of the flexible pouch 240 holds and encompasses the diaphragm chamber 214 in its entirety. Accordingly, to properly accommodate and position the diaphragm chamber in its intended function, the front wall 242 contains an open portal 260 whose diameter and configuration is coextensive with the inlet 224 and inlet closure 226 of the diaphragm chamber 214. As shown by FIG. 9 in particular, the inlet 224 and closure 226 are visible and extend through the portal 260 of the front wall 242. In this manner, any and all fluid fecal matter passing through the portal 260 immediately enters the interior of the housing 216 of the diaphragm chamber 214 as it proceeds before passing into the remainder of the interior volume 250 within the flexible pouch/bandage 240. In this construction, therefore, no fluid matter can enter the interior of the flexible pouch without first passing through the diaphragm chamber 214.

Figure 12:
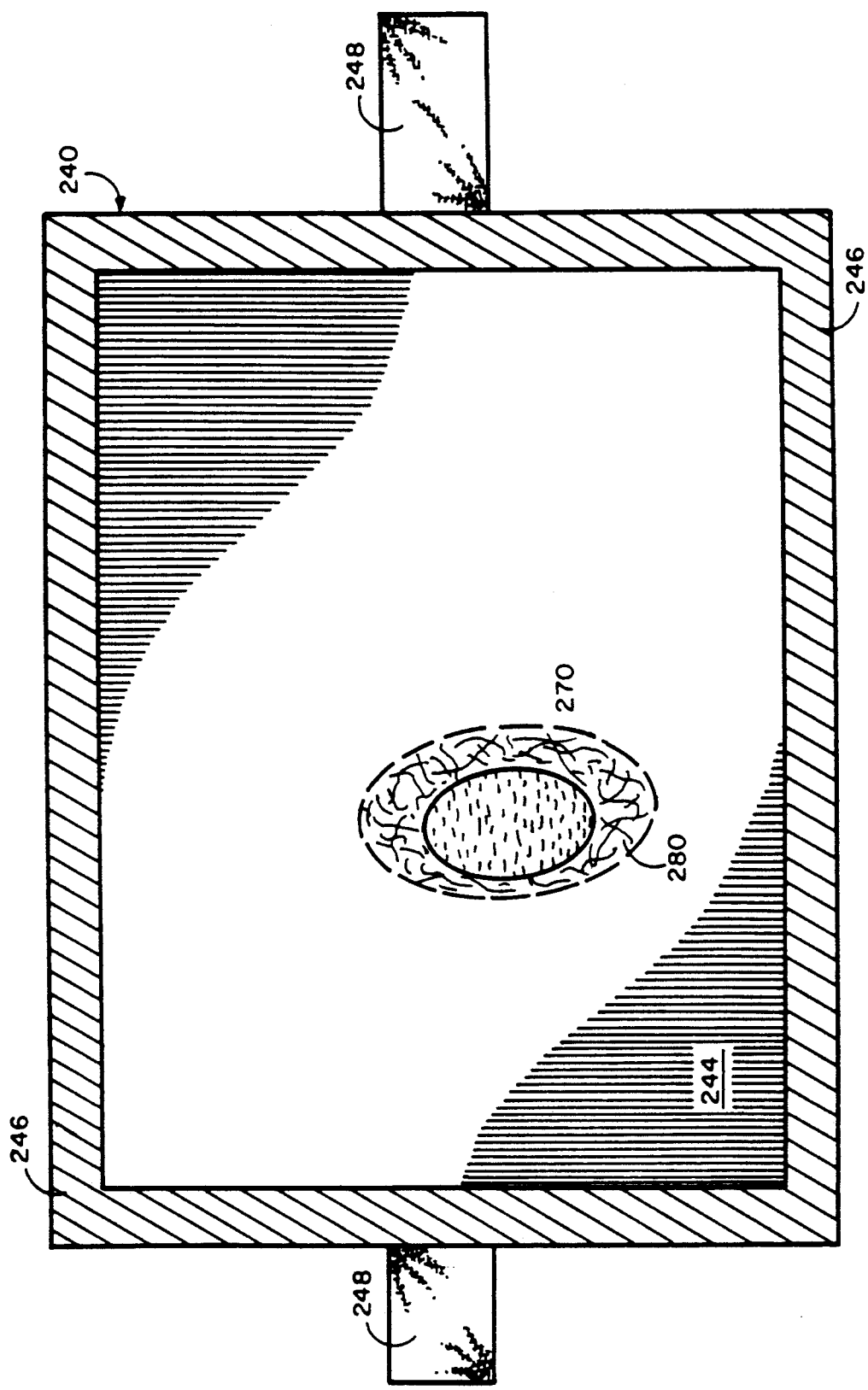
FIG. 12 is a rear view of the fluid fecal matter receiving system of FIGS. 7-11.

The rear wall 244 is illustrated by FIG. 12 and includes at least one gas permeable and liquid impermeable porous membrane 270 which is joined directly to and thus forms an integral part of the rear wall itself. The porous membrane 270 provides a plurality of external and interior membrane surfaces through its thickness; and has the property of allowing the passage of gases land vapors while prohibiting the passage of liquids or solids. Such porous membranes are deemed "gas permeable"; and are commercially available. It will be appreciated that a variety of different compositions and constructions of such gas permeable porous membranes are known including organic and inorganic substances individually and in mixture. For purposes of the present invention, the true composition and mode of preparation for the membrane material, the true pore size, the total porosity and void volume, and the degree to which gases are permitted to pass through the membrane is of no importance or consequence whatsoever. To the contrary, so long as gaseous fecal materials are permitted to pass through the porous membrane and released from the interior of the flexible pouch/bandage via the porous membrane while concurrently prohibiting and retaining all liquids and/or solids, all such gas permeable/liquid impermeable porous membranes are deemed to be within the scope of the present invention.

In addition, within the internal volume 250 of the flexible pouch bandage 240; and filling in particular the volume space between the back plate 220 and netting 232 of the diaphragm chamber 214 and the gas permeable porous membrane 270 of the rear wall 244 of the flexible pouch 240; is a quantity of a superabsorbent fibrous material 280 which is able to absorb at least 15 times, and preferably 60-100 times its own weight of liquid. The majority of the interior volume 250 of the flexible pouch/bandage 240 is thus at least partially, and preferably entirely filled, with the superabsorbent fibrous material 280. In this manner, any and all liquid fecal material coming into contact with the internal volume of the flexible pouch is absorbed at least partially if not entirely by the superabsorbent fibrous material 280.

Having described each of the component parts of the fluid fecal matter receiving system individually, it is deemed for purposes of clarity and comprehensive understanding to follow the course and flow of fecal material discharged from the living subject into the receiving system. Accordingly, the resected bowel end 200 is placed through the bowel retaining ring 212 as illustrated by FIG. 7. Clearly, there is expected to be a minimal length of resected bowel for this purpose; and the bowel retaining ring 212 typically will be positioned adjacent to and abutt the side of the living subject. The flexible pouch/bandage 240 encompassing and containing the diaphragm chamber 214 is then joined to the bowel retaining ring 212 in the manner shown by FIG. 10. As seen therein, the resected bowel end 200 penetrates and extends partially into the diaphragm chamber and thus concomitantly enters into the interior volume of the flexible pouch. Physical juncture is made via the inlet 224 and closure 226 of the diaphragm chamber which are disposed upon and attached to the bowel retaining ring 212 thereby forming a fluid-tight connection. The straps 248 of the flexible pouch 240 are desirably tied snuggly around the body of the living subject such that firm abuttment and close proximity without major movement are maintained between the resected bowel end of the living subject and the whole of the fluid fecal matter receiving system 210.

Fluid fecal matter discharged through the alimentary canal of the bowel flows through the resected bowel end 200 which is in fluid flow communication directly with the housing 216 of the diaphragm chamber 214. The netting 232 of the diaphragm chamber separates the liquid and gaseous fecal constituents; and retains the solid fecal material entering the diaphragm chamber such that the retained solid fecal material is held partially within the housing 216 and partially within the lumen of the resected bowel itself. The separated liquid and gaseous constituents of the fluid fecal matter fractioned by the netting 232 tend to flow in different and alternative directions. The gaseous fecal material, once separated, tends to flow directly through the netting through the outlet 228 of the diaphragm chamber 214 and then encounters the superabsorbent fibrous material 280 filling the interior volume of the flexible pouch/bandage 240. The superabsorbent fibrous material 280 - being itself porousn allows and permits the fecal gases to pass directly through until the gases reach the rear wall 244 and the gas permeable porous membrane 270. Typically, however, some, but not all, of the gaseous fecal material will then pass through the porous membrane 270 into the ambient environment. The residual portion of the gaseous fecal material then remaining within the internal volume 250 of the flexible pouch 240 are temporarily contained within the superabsorbent fibrous material 280. However, when the person moves, walks, or sits down, the movement and/or weight of the person will be thrust directly against the internal contents of the flexible pouch/bandage—thereby forcing the residual gaseous fecal material through the porous membrane 270 under considerable compression force. In this manner, substantially all of the gaseous fecal material separated by the diaphragm chamber 214 is released ultimately over time into the ambient environment.

The liquid fecal material separated by the netting 232 of the diaphragm chamber 214 is directed through the housing 216 and flows through the apertures 230 into the rest of the internal volume of the flexible pouch/bandage 240. The separated liquid fecal material passing through the apertures 230 thus come into direct and intimate contact with the superabsorbent fibrous material 280 filling the interior volume of the flexible pouch; and the liquid fecal material becomes absorbed at least in part (if not entirely) by the superabsorbent fibrous material. Similarly, when the person moves, walks, or sits down, the body of the person presses against and consequently compresses the housing 216 of the diaphragm chamber 214—thereby forcing the separated liquid fecal material to pass by compression force through the apertures 230 and also through the outlet 228 of the housing into the volume space filled by the superabsorbent fibrous material 280. In this manner, the separated liquid is periodically expelled from the diaphragm housing 214 under compression force by the normal movements of the living subject; and is quickly absorbed by the superabsorbent fibrous material as a consequence. Moreover, when the person rises or markedly changes position, the housing 216 then expands back into its original volume and configuration; and again provides a greater capacity for additional fluid fecal matter to be received, separated, and collected by the receiving system.

It will be appreciated in particular that the compressible and expandable housing 216, the apertures 230, and the netting 232 collectively provide and serve as the fluid-modulating element of the diaphragm chamber 214 in this embodiment. Thus, all fluid fecal material flowing from the resected bowel end of the living subject is acted upon by the diaphragm chamber 214 to yield a resulting fecal fluid product—which is collectively the separated and retained solid fecal material; the separated and subsequently absorbed liquid fecal material; and the separated gaseous fecal material subsequently released into the ambient environment. Moreover, it will be recognized that the variable chamber 214 is an essential component positioned within the internal volume of the flexible pouch itself. Thus, in this fluid fecal matter receiving system, when the receiver is periodically replaced, the modulator unit itself is concomitantly replaced as well.

Furthermore, in this embodiment, recognizing that fecal matter—whether gaseous, liquid, or solid—is malodorous if not actually organically offensive, it is most desirable that one or more gas-deodorant compositions optionally be added to the superabsorbent fibrous material within the internal volume of the flexible pouch/bandage. These gas-deodorant compositions would therefore serve two different functions and purposes. First, these substances would deodorize such gaseous fecal material as is released from the diaphragm chamber and passes through the superabsorbent fibrous material prior to being released into the ambient environment via the gas permeable porous membrane. The release of a deodorized gas would be very socially desirable and pleasant for the living subject. Second, the deodorization of the liquid fecal materials absorbed by the superabsorbent fibrous material would minimize the presence of malodorous substances retained within the flexible pouch/bandage. The presence of deodorizing agents would reduce is the discomfort typically experienced by the living subject as a result of wearing and using conventionally known ileostomy/colostomy bags.

Finally, it will be perceived and acknowledged that this fluid fecal matter receiving system as a whole affirmatively answers and successfully resolves the two fundamental issues underlying and determining the true use and value of such systems. First, this fluid fecal matter receiving system provides for the receipt, collection, separation, and ultimate disposal of fecal matter without any person being placed at risk or becoming detrimentally affected by the fecal matter. Second, this fluid fecal matter receiving system performs the effective receipt, collection, and disposal of fluid fecal matter without meaningfully influencing, contaminating, or seriously altering the health and medical status of the ileostomy/colostomy patient from whom the fecal matter must be removed. Thus, the present system is demonstrably different and distinguishable from its predecessors by virtue of these singular achievements.

D. A System For Receiving A Hazardous/Toxic Fluid From An Inanimate Source

Figure 13:
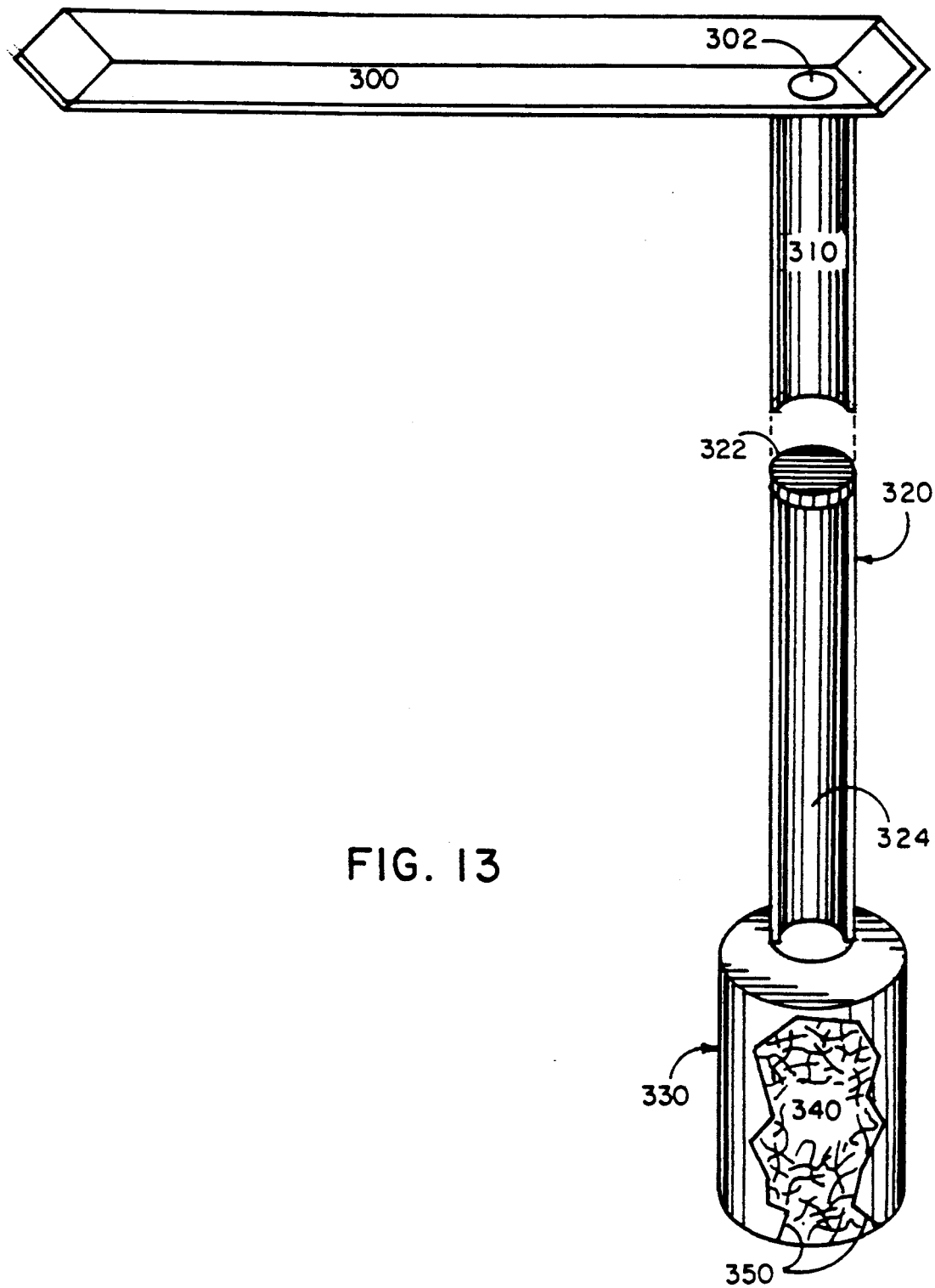
FIG. 13 is a perspective view of a hazardous/toxic fluid receiving system.

A closed, fluid-modulating system for receiving and collecting a hazardous/toxic fluid from an inanimate source is illustrated by FIG. 13. By definition, a hazardous fluid is a substance which poses potential danger to the health and safety of the public because of its inherent properties. Substances are considered hazardous if they are irritating, corrosive, flammable, capable of producing combustible vapors, pyrophoric, unstable, or capable of rapid release of energy. The term includes wastes, chemicals, and materials generally without regard to composition. In comparison, a toxic fluid represents the lethal capacity of a substance and is recognized by its capacity to cause tissue damage, disease, or death to a living subject. The degree of toxicity depends on the dosage and route of exposure of the substance (whether by ingestion, inhalation, or through contact with the skin). Acute toxicity refers to the effects of a single intense exposure; whereas chronic toxicity refers to the cumulative effect of repeated exposure to various amounts of the agent over a longer time frame. For purposes of the present invention, the terms hazardous and toxic are used interchangably while retaining their individual connotative and denotative meanings.

The embodiment of the present invention which is a hazardous/toxic fluid receiving system comprises: a conduit formed as a non-reactive pipe for conveying a hazardous/toxic fluid from its source; a discrete modulator unit formed as a one-way flow-through union disposed at one open end of the pipe and being in fluid flow communication with the source of the hazardous/toxic fluid; and a receiver of determinable dimensions and volume in the form of a holding tank capable of being placed in fluid flow communication with the pipe via the union, at least one superabsorbent fibrous material being disposed within the holding tank for absorbing such fluid as flows into the holding tank.

The typical use circumstances and applications for this embodiment of the present invention are particularly desirable in pathology laboratories of hospitals, mortuaries, dry cleaning establishments and processing factories, and any other site or place where hazardous or toxic fluid materials are employed. In the pathology laboratory and the mortuary, formaldehyde, typically in the form of aqueous formalin, is frequently employed both as a preservative and as a disinfecting agent. formaldehyde and formalin are recognized hazardous chemicals whose collection and disposition is now being regulated by various state and federal agencies. Similarly, in far more commonplace situations as the dry cleaning industry, a variety of different toxic fluids such as methylene chloride, chloroform, carbon tetrachloride, and various other ketones and benzene derivatives are employed routinely. All these agents are recognized toxic fluids; and their handling as well as their collection and disposal is a matter of the greatest importance to the health and safety of the public at large as well as to the workers in the industry.

For purposes of describing the present embodiment, therefore, a single use situation will be described which for illustrative purposes only will be limited to the use of formalin as a preservative in the mortuary and funeral industry. Accordingly, as seen in FIG. 13, a shallow embalming table 300 for holding the corpse or other remains of a subject is constructed in fluid flow communication with the hazardous/toxic receiving system comprising the present invention. The table 300 is generally an open volumetric container having a sieve 302 for drainage of fluids. Typically, the corpse is placed on the table 300 and his bodily fluids drained and replaced by a formalin solution. All the drained body fluids as well as a certain quantity of the aqueous formalin are contained within the embalming table and flow through the sieve into the receiving system.

Directly joined to the embalming table 300 and the sieve 302 is a conduit formed as a non-reactive pipe 310. One open end of the pipe 310 is joined directly to the table 300 via the sieve 302. The other open end of the pipe 310 is in direct fluid communication with a discrete modulator unit formed as a one-way, flow-through union 320 disposed at the other open end of the pipe.

The union is in fluid flow communication, therefore, with the table 300 and the corpse which is being filled with aqueous formalin prior to burial. The union comprises a porous matrix layer 322 which occludes the entirety of the open end of the pipe 310; and a connector 324 which serves as the means for fluid flow communication between the porous matrix layer 322 and the remainder of the receiving system. As previously described and employed in earlier embodiments herein, the porous matrix layer 322 has a plurality of external and internal matrix surfaces such that the hazardous/toxic fluid can pass through the porous matrix layer as a resulting fluid product while the ambient environment can not pass through the thickness of the porous matrix layer. The connector 324 is desirably a cylindrical-shaped article and preferably has screw threads at either end such that a fluid-tight juncture can be made with the pipe 310 and the subsequently positioned replaceable receiver.

An optional, but often highly desirable, feature not illustrated within FIG. 13 is the addition and presence of a unidirectional flow valve which allows the resulting fluid product to pass through while prohibiting any back flow of the fluid product. When present, this unidirectional flow valve would be positioned in-line below the porous matrix layer 322 and preferably housed within the connector 324. It will be recognized, however, that this is merely an optional feature to further protect the security of the persons working in this environment.

Another optional feature to be employed in combination with the flow-through union 320 is the optional inclusion and use of one or more chemical reactants or reagents which would react in a recognized manner with the aqueous formalin either before or after its passage through the porous matrix layer 322. In these circumstances, it is often desirable to dispose the chemical reagent or reactant directly upon the external and internal surfaces of the porous matrix layer itself in a conventionally known manner. This would provide not only a useful positional site for the chemical substance but also provide a physical support for the chemical action to proceed while the fluid travels through the external and internal surfaces of the matrix layer itself.

The third essential component of this embodiment is the replaceable receiver which is formed as a holding tank 330 and is in fluid flow communication with the union 320, the pipe 310, and the tub 300. The holding tank 330 appears as a large capacity drum within FIG. 13; and is constructed of resilient material in substantially cylindrical configuration having a typical 55 gallon volume. Alternatively, the holding tank may take form as any configuration of determinable dimensions and provide any volume which is desirable or useful for that particular application.

The holding tank comprises a container which serves as the tangible means for receiving and collecting the resulting fluid product released from the union; and at least one superabsorbent fibrous material filling the internal volume of the holding tank at least in part and able to absorb at least 15 times its own weight of liquid. An optional but highly desirable feature of this embodiment is the presence also of at least one recognized neutralizing agent within the holding tank for at least partial neutralization of such resulting fluid product as is absorbed by the superabsorbent fibrous material.

As seen within FIG. 13, the holding tank 330 comprises the cylindrical-shaped container 340 which is at least partially filled with a superabsorbent fibrous material 350. The optional but highly desirable neutralizing agent is dispersed within the internal volume of the container 340; and lies intermixed with the superabsorbent fibers within the holding tank proper. Since the hazardous/toxic fluid for illustrative purposes is aqueous formalin which passes through the porous matrix layer as a resulting fluid product; and becomes subsequently absorbed (at least in part if not in its entirety) by the superabsorbent fibrous material,, it is desirable to include two different chemical agents within the holding tank for purposes of achieving at least partial neutralization. These chemical agents desirably are hydrogen peroxide and sodium carbonate. The interaction of these chemical agents with the resulting fluid product would chemically alter and at least partially neutralize the hazardous/toxic properties of the formalin in comparison to those recognized in its original, unaltered state.

In this manner, any and all formalin as well as other tissue fluids removed from the corpse lying within the embalming table flows directly through the pipe 310 and the porous matrix layer 322 of the union 320 for subsequent receipt and collection by the holding tank 330. The superabsorbent fibrous material 350 within the holding tank then absorbs most if not all of the formalin; and, given the presence of one or more optional neutralizing agents, is able to at least partially neutralize the hazardous and toxic properties of the ultimately absorbed fluid product. The holding tank 330, being replaceable, may then be removed as needed or desired by the user for final disposition in an approved manner. During the replacement of the holding tank, the presence of the porous matrix layer 322 prevents the ambient environment from passing through the totality of the receiving system and thus enhances and ensures the safety and protection of the persons working in the mortuary or funeral home.

Thus, the present hazardous/toxic fluid receiving system directly addresses and satisfactorily resolves the two fundamental underlying issues. First, this receiving system provides for the receipt, collection, and subsequent disposal of hazardous and/or toxic fluids without any person being placed at serious risk or becoming detrimentally affected by the fluids. Second, the present receiving system performs the effective receipt, collection, and disposal of hazardous and/or toxic fluids without meaningfully influencing, contaminating, or otherwise altering the source from which the fluids originate. These attributes and achievements clearly separate and distinguish the present system from any and all superficially similar processes and apparatus.

The present invention is not to be restricted in form nor limited in scope except by the claims appended hereto.

What I claim is:

1. A closed, fluid-modulating receiving system for the conveyance, modulation, and collection of fluid matter from its source, said fluid-modulating receiving system comprising:

an external conduit for the closed conveyance of fluid matter from its source, said conduit having a closed body, an internal lumen, and two discrete ends, wherein one of said conduit ends is to be positioned internally within and lie in closed fluid flow communication with the source of fluid matter and the other of said conduit ends is to extend externally from said source and lie in the ambient environment;

a discrete, flow-through modulator unit positioned away from the source of fluid matter and being in closed fluid flow communication with said internal lumen and said external end of said conduit such that said modulator unit prevents the ambient environment from passing therethrough into the internal lumen of said conduit, said modulator unit comprising at least one fluid-modulating element, a flow inlet, and a flow outlet and (a) wherein all fluid matter conveyed from the source by said conduit flows into reactive engagement with and is acted upon by said modulator unit without concomitant exposure to the ambient environment, and (b) wherein all fluid matter conveyed from the source by said conduit flows into reactive engagement with and is acted upon by said modulator unit without concomitant release of said fluid matter in whole or in part to the ambient environment and (c) wherein at least one identifiable physical or chemical property of said fluid matter is reactively engaged and acted upon by said modulator unit without concomitant exposure or release to the ambient environment to yield a resulting fluid product;

connecting means in closed fluid flow communication with said modulator unit and said conduit; and a closed receiver of fixed dimensions and internal volume which is removable on-demand from said connecting means and said modulator unit and replaceable at will, said closed receiver being positioned in closed fluid flow communication with said modulator unit via said connecting means for collection of said resulting fluid product, the internal volume of said receiver being not less than partially filled with at least one superabsorbent fibrous material comprising fluid-absorbing fibers which absorb at least 15 times their own weight of liquid, such resulting fluid product as passes in closed fluid flow from said modulator unit via said connecting means into said receiver being at least partially absorbed by said superabsorbent material.

2. A closed, fluid-modulating receiving process for the conveyance, modulation, and collection of fluid matter from its source, said fluid-modulating receiving process comprising the step of:

assembling an apparatus comprising (a) an external conduit for the closed conveyance of fluid matter from its source, said conduit having a closed body, an internal lumen, and two discrete ends, wherein one of said conduit ends is to be positioned internally within and lie in closed fluid flow communication with the source of fluid matter and the other of said conduit ends is to extend externally from said source and lie in the ambient environment;

(b) a discrete, flow-through modulator unit positioned away from the source of fluid matter and being in closed fluid flow communication with said internal lumen and said external end of said conduit such that said modulator unit prevents the ambient environment from passing therethrough into the internal lumen of said conduit, said modulator unit comprising at least one fluid-modulating element, a flow inlet, and a flow outlet and (i) wherein all fluid matter conveyed from the source by said conduit flows into reactive engagement with and is acted upon by said modulator unit without concomitant exposure to the ambient environment, and (ii) wherein all fluid matter conveyed from the source by said conduit flows into reactive engagement with and is acted upon by said modulator unit without concomitant release of said fluid matter in whole or in part to the ambient environment and (iii) wherein at least one identifiable physical or chemical property of said fluid matter is reactively engaged and acted upon by said modulator unit without concomitant exposure or release to the ambient environment to yield a resulting fluid product;

(c) connecting means in closed fluid flow communication with said modulator unit and said conduit; and (d) a closed receiver of fixed dimensions and internal volume which is removable on-demand from said connecting means and said modulator unit and replaceable at will, said closed receiver being positioned in closed fluid flow communication with said modulator unit via said connecting means for collection of said resulting fluid product, the internal volume of said receiver being not less than partially filled with at least one superabsorbent fibrous material comprising fluid-absorbing fibers which absorb at least 15 times their own weight of liquid, such resulting fluid product as passes in closed fluid flow from said modulator unit via said connecting means into said receiver being at least partially absorbed by said superabsorbent material;

positioning said assembled apparatus in closed fluid flow communication with the source of the fluid matter; and allowing the fluid matter to flow from the source into said assembled apparatus.

* * * * *